(12) United States Patent
Davenport

(10) Patent No.: US 8,926,445 B2
(45) Date of Patent: *Jan. 6, 2015

(54) GOLF FREE SWING MEASUREMENT AND ANALYSIS SYSTEM

(71) Applicant: Roger Davenport, Fort Lauderdale, FL (US)

(72) Inventor: Roger Davenport, Fort Lauderdale, FL (US)

(73) Assignee: Golf Impact, LLC, Fort Lauderdale, FL (US)

(*) Notice: Subject to any disclaimer, the term of this patent is extended or adjusted under 35 U.S.C. 154(b) by 0 days.

This patent is subject to a terminal disclaimer.

(21) Appl. No.: 13/868,078

(22) Filed: Apr. 22, 2013

(65) Prior Publication Data

US 2014/0073446 A1 Mar. 13, 2014

Related U.S. Application Data

(63) Continuation-in-part of application No. 13/290,124, filed on Nov. 6, 2011, now Pat. No. 8,425,340, which is a continuation-in-part of application No. 13/225,433, filed on Sep. 3, 2011, now Pat. No. 8,221,257.

(51) Int. Cl.
*A63B 69/36* (2006.01)
*A63B 57/00* (2006.01)
*A63B 24/00* (2006.01)
*A63B 71/06* (2006.01)

(52) U.S. Cl.
CPC ....... *A63B 24/0003* (2013.01); *A63B 2220/833* (2013.01); *A63B 2220/40* (2013.01); *A63B 24/0006* (2013.01); *A63B 71/0619* (2013.01); *A63B 69/3632* (2013.01); *A63B 57/00* (2013.01)

USPC .......... 473/223; 473/219; 473/221; 473/266; 473/409; 434/252; 273/108.2

(58) Field of Classification Search
USPC ......... 473/131, 150–154, 199, 219–223, 266, 473/342, 409; 463/3, 36–39; 434/252; 273/108.2; 702/41
See application file for complete search history.

(56) References Cited

U.S. PATENT DOCUMENTS

| | | | | |
|---|---|---|---|---|
| 3,792,863 A * | 2/1974 | Evans | | 473/223 |
| 5,469,175 A * | 11/1995 | Boman | | 342/357.52 |
| 6,224,493 B1 * | 5/2001 | Lee et al. | | 473/223 |
| 6,441,745 B1 * | 8/2002 | Gates | | 340/669 |
| 7,264,555 B2 * | 9/2007 | Lee et al. | | 473/223 |
| 7,672,781 B2 * | 3/2010 | Churchill et al. | | 701/468 |
| 7,801,575 B1 * | 9/2010 | Balardeta et al. | | 455/574 |
| 7,871,333 B1 * | 1/2011 | Davenport et al. | | 473/223 |

(Continued)

*Primary Examiner* — Milap Shah
(74) *Attorney, Agent, or Firm* — Clayton, McKay & Bailey, PC

(57) ABSTRACT

The presented invention relates to a method for determining the effectiveness of a golfer's swing without the requirement of the club head making contact with a golf ball. More specifically, the present invention relates to a measurement and analysis system comprising a first module that attaches to the club head and captures measurement receiver signal strength data during the entire swing time line and may capture motional data on same time line, further first module wirelessly communicates bi-directionally with a second module that is further connected to a user interface device and computational engine where feedback results are derived and conveyed to the golfer. The system provides comprehensive feedback for a swing characterization time line referenced to the spatial domain using receiver signal strength measurements that may be in combination with motional and dynamics orientation measurements.

17 Claims, 21 Drawing Sheets

(56) References Cited

U.S. PATENT DOCUMENTS

| | | | |
|---|---|---|---|
| 8,210,960 B1 * | 7/2012 | Davenport | 473/223 |
| 8,221,257 B2 * | 7/2012 | Davenport | 473/223 |
| 8,414,411 B2 * | 4/2013 | Stites et al. | 473/221 |
| 8,425,340 B2 * | 4/2013 | Davenport | 473/223 |
| 2002/0077189 A1 * | 6/2002 | Tuer et al. | 473/151 |
| 2004/0259651 A1 * | 12/2004 | Storek | 473/131 |
| 2005/0013467 A1 * | 1/2005 | McNitt | 382/107 |
| 2005/0032582 A1 * | 2/2005 | Mahajan et al. | 473/222 |
| 2005/0215335 A1 * | 9/2005 | Marquardt | 473/131 |
| 2005/0215340 A1 * | 9/2005 | Stites et al. | 473/233 |
| 2006/0128503 A1 * | 6/2006 | Savarese et al. | 473/353 |
| 2008/0085778 A1 * | 4/2008 | Dugan | 473/223 |
| 2009/0111602 A1 * | 4/2009 | Savarese et al. | 473/283 |
| 2010/0222152 A1 * | 9/2010 | Jaekel et al. | 473/223 |
| 2011/0086720 A1 * | 4/2011 | Jaekel et al. | 473/223 |
| 2012/0322569 A1 * | 12/2012 | Cottam | 473/223 |

* cited by examiner

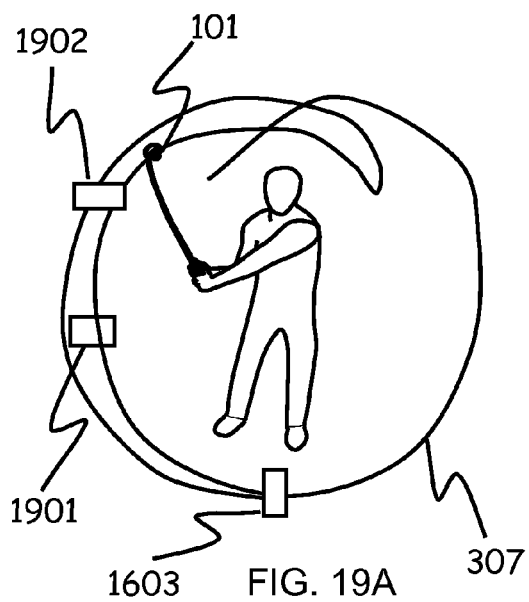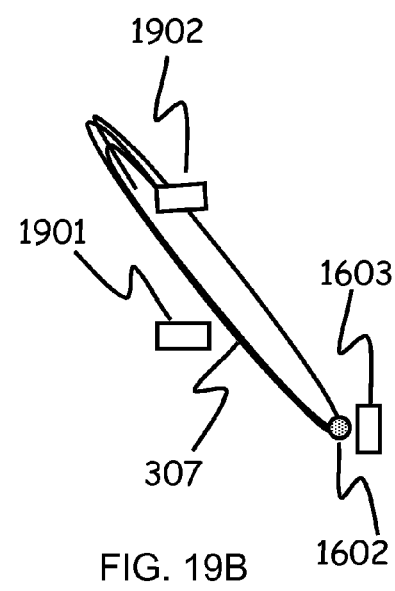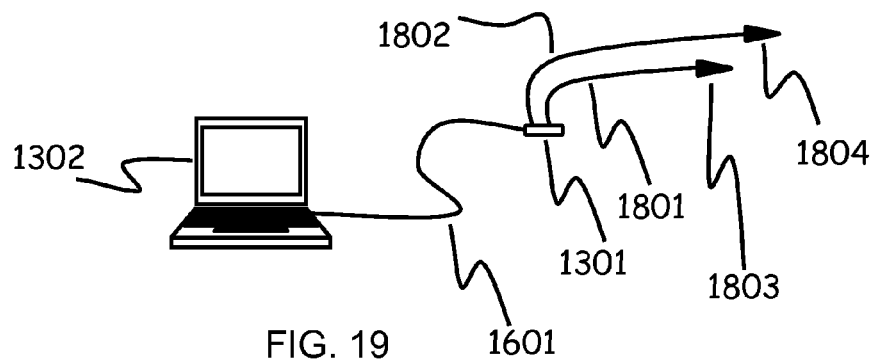

GOLF FREE SWING MEASUREMENT AND ANALYSIS SYSTEM

CROSS REFERENCE TO RELATED APPLICATION

This patent application is a continuation-in-part application of U.S. patent application Ser. No. 13/290,124 filed on Nov. 6, 2011, now U.S. Pat. No. 8,425,340, entitled "Golf Free Swing Measurement and Analysis System", which is a continuation-in-part of U.S. patent application Ser. No. 13/225,433 filed on Sep. 3, 2011, now U.S. Pat. No. 8,221,257, entitled "Golf Free Swing Measurement and Analysis System" that are both incorporated herein by reference.

FIELD OF THE INVENTION

The presented invention relates to a method for determining the effectiveness of a golfers swing without the requirement of the club head making contact with a golf ball. More specifically, the present invention relates to a system comprising a first module that attaches to the club head and captures measurement data and relative position data during the entire swing, further first module wirelessly communicates bi-directionally with a second module that is further connected to a user interface device and computational engine where feedback results are calculated and conveyed to the golfer. The system provides comprehensive feedback for swing characterization for detailed swing timing results, dynamic club head orientation and motion metrics and dynamics shaft actions all referenced to the spatial domain.

BACKGROUND OF THE INVENTION

There are numerous prior art external systems disclosures using video and or laser systems to analyze the golf swing. There are also numerous golf club attached systems using shaft mounted strain gauges and or single to multiple accelerometers and gyros to calculate golf swing metrics. However, none of these prior art approaches contemplate a mobile system with sensors attached to the club head and use receiver signal strength measurements to correlate time line measurements with the spatial domain for the non-linear travel path of the club head during a golf swing.

U.S. Pat. No. 3,945,646 to Hammond integrates three-dimensional orthogonal axes accelerometers in the club head, and describes a means for wirelessly transmitting and receiving the resulting sensor signals. However, he does not contemplate the computational algorithms involving the multi-lever mechanics of a golf club swing required to solve for all the angles of motion of the club head during the swing with a varying swing radius. His premise of being able to obtain face angle only with data from his sensors 13, and 12 (x and y directions respectively described below) is erroneous, as for one example, the toe down angle feeds a large component of the radial centrifugal acceleration onto sensor 12 which he does not account for. He simply does not contemplate the effects of the dynamically changing orientation relationship between the inertial acceleration forces and the associated coordinate system acting on the club head constrained by the multi-lever golf swing mechanics and the fixed measurement coordinate system of the three orthogonal club head sensors.

U.S. Pat. No. 7,672,781 to Churchill uses receiver signal strength measurements with multiple directional antennas in combination with linear calculation methods based on acceleration measurements to determine the location of a movable bodies that could be a golf club. Churchill fails to contemplate using RSSI measurements without the use of directional sectorized antennas in combination with sensors measurements analysis applied to a movable object with non-linear travel.

The prior art disclosures fail to teach a golf free swing analysis system that measures receiver signal strength at the club head that defines a swing time line of the non-linear club head travel path for the entire swing that is associated and referenced to the spatial domain. Further, the receiver signal strength time line may be used in association with synchronized motional sensor measurements also taken at the club head to define the swing characteristics of nonlinear travel path of the club head referenced to the locations(s) in spatial domain for the entire non-impact swing.

BRIEF SUMMARY OF THE INVENTION

The present invention is a golf swing measurement and analysis system that measures directly and stores time varying acceleration forces during the entire golf club swing. The measurement and analysis system comprises four major components; a golf club, a club head module (first module) that is attachable to and removable from the club head, a second module that is located and a predetermined location and a computer program. The golf club comprises a shaft and a club head with the club head comprising a face and a top surface where the module is attached. The first module comprise a means to measure acceleration separately on three orthogonal axes, and first module or second module or both modules have a means of measuring receiver signal strength. First module and second module have means to communicate wirelessly and second module has a means to transport the measured data to a computer or other smart device where the computer program resides. The computer program comprises computational algorithms for calibration of data and calculation of golf metrics described on a time line and further correlation of that time line to the spatial domain, and support code for user interface commands and inputs and visual display of the metrics.

During operation the module is attached on the head of the golf club, and during the entire golf swing it captures data from the three acceleration sensors axes. The acquired swing measurement data is either stored in the module for later analysis or transmitted immediately from the module to a receiver with connectivity to a computation engine. A computational algorithm that utilizes the computational engine is based on a custom multi-lever golf swing model utilizing both rigid and non-rigid levers. This algorithm interprets the measured sensor data to determine the dynamically changing relationship between an inertial coordinates system defined by the multi-lever model for calculation of inertial acceleration forces and the module measurement axes coordinate system attached to the club head. Defining the dynamically changing orientation relationship between the two coordinate systems allows the interpretation of the measured sensor data with respect to a non-linear travel path allowing the centrifugal and linear acceleration components to be separated for each of the module's three measured axes. Now with each of the module axes measurements defined with a centrifugal component (also called the radial component), and a linear spatial transition component the swing analysis system accurately calculates a variety of golf swing metrics which can be used by the golfer to improve their swing. These swing quality metrics include:

1. Golf club head time varying velocity for a significant time span before and after maximum velocity of the swing.

2. Time varying swing radius for a significant time span before and after maximum velocity of the swing.
3. Golf club head face approach angle of the golf club head, whether the club face is "open", "square", or "closed", and by how much measured in degrees, for a significant time span before and after maximum velocity of the swing.
4. Wrist cock angle during the swing, for a significant time span before and after maximum velocity of the swing.
5. Club shaft lag/lead flexing during the swing, for a significant time span before and after maximum velocity of the swing.
6. Club head toe down angle during the swing, for a significant time span before and after maximum velocity of the swing.
7. Club head acceleration force profile for the backswing that include time varying vector components and total time duration.
8. Club head acceleration force profile for the pause and reversal segment of the swing after backswing that includes time varying vector components and total time duration.
9. Club head acceleration force profile for the power-stroke after pause and reversal that includes time varying vector components and total time duration.
10. Club head acceleration force profile for the follow through after power-stroke that includes time varying vector components and total time duration.
11. Club head swing tempo profile which includes total time duration of tempo for the backswing, pause and reversal, and power-stroke and provides a percentage break down of each segment duration compared to total tempo segment duration.
12. All analysis metrics listed above correlated to the spatial domain.

The module acceleration measurement process comprises sensors that are connected to electrical analog and digital circuitry and an energy storage unit such as a battery to supply power to the circuits. The circuitry conditions the signals from the sensors, samples the signals from all sensors simultaneously, converts them to a digital format, attaches a time stamp to each group of simultaneous sensor measurements, and then stores the data in memory. The process of sampling sensors simultaneously is sequentially repeated at a fast rate so that all acceleration forces profile points from each sensor are relatively smooth with respect to time. The minimum sampling rate is the "Nyquist rate" of the highest significant and pertinent frequency domain component of any of the sensors' time domain signal.

The sensor module also contains circuitry for storing measured digital data and a method for communicating the measured data out of the module to a computational engine integrated with interface peripherals that include a visual display and or audio capabilities. In the preferred embodiment the club head module also contains RF circuitry for instant wireless transmission of sensor data immediately after sampling to a RF receiver plugged into a USB or any other communications port of a laptop computer. The receiver comprises analog and digital circuitry for receiving RF signals carrying sensor data, demodulating those signals, storing the sensor data in a queue, formatting data into standard USB or other communication formats for transfer of the data to the computation algorithm operating on the computation engine.

An alternate embodiment of this invention contemplates a similar module without the RF communication circuitry and the addition of significantly more memory and USB connectivity. This alternate embodiment can store many swings of data and then at a later time, the module can be plugged directly into to a USB laptop port for analysis of each swing.

Another alternate embodiment of this invention contemplates a similar club head module without the RF circuitry and with a wired connection to a second module mounted on the shaft of the club near the grip comprising a computational engine to run computational algorithm and a display for conveying golf metrics.

BRIEF DESCRIPTION OF DRAWINGS

The above and other features of the present invention will become more apparent upon reading the following detailed description in conjunction with the accompanying drawings, in which:

FIGS. 11, 11A and 11B, shows the possible club head module mounting angle error $\lambda$ that is detected and then calibrated out of the raw data.

FIGS. 12, 12A and 12B, shows another club head module mounting angle error that is detected and then calibrated out of the raw data.

FIGS. 19, 19A and 19B show the system setup, a configuration example option and operation of the third embodiment of the time space correlation.

DETAILED DESCRIPTION OF A PREFERRED EMBODIMENT

Figure 1:
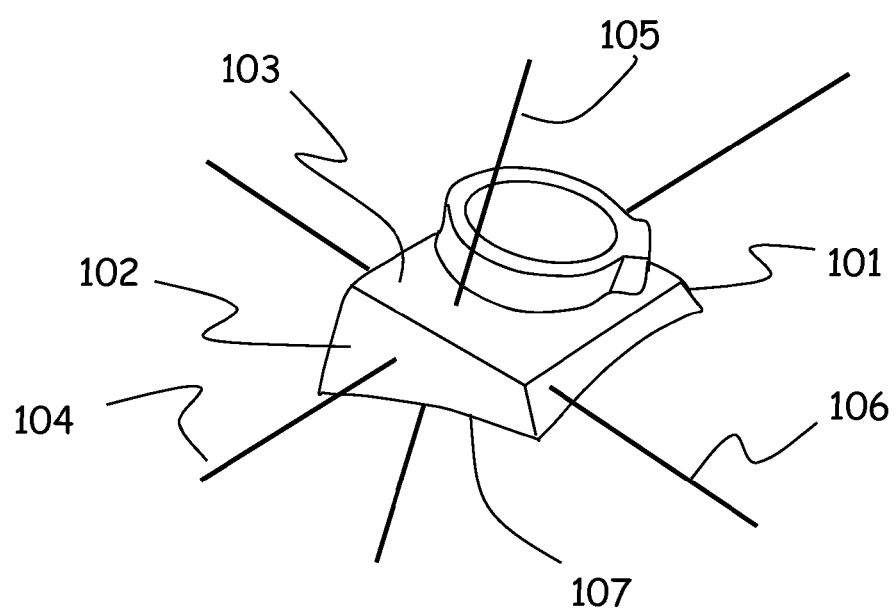
FIG. 1 is a perspective view of the present invention embodied with an attached module that contains three acceleration sensors located on a three-dimensional orthogonal coordinate system with axes $x_f$, $y_f$, and $z_f$, where the axes are fixed with respect to the module.

The present invention comprises accelerometers attached to the club head that allow the motion of the club head during the swing to be determined. In the preferred embodiment as shown in FIG. 1 sensors are incorporated in a club head attachable module 101. The module 101 has a front surface 102 and a top surface 103 and an inwardly domed attachment surface 107. The sensors in module 101 measure acceleration in three orthogonal axes which include: the $x_f$-axis 104 that is perpendicular to the front surface 102, the $z_f$-axis 105 that is perpendicular to $x_f$-axis 104 and perpendicular to the top surface 103 and the $y_f$-axis 106 that is perpendicular to both the $x_f$-axis 104 and the $z_f$-axis 105.

Figure 2:
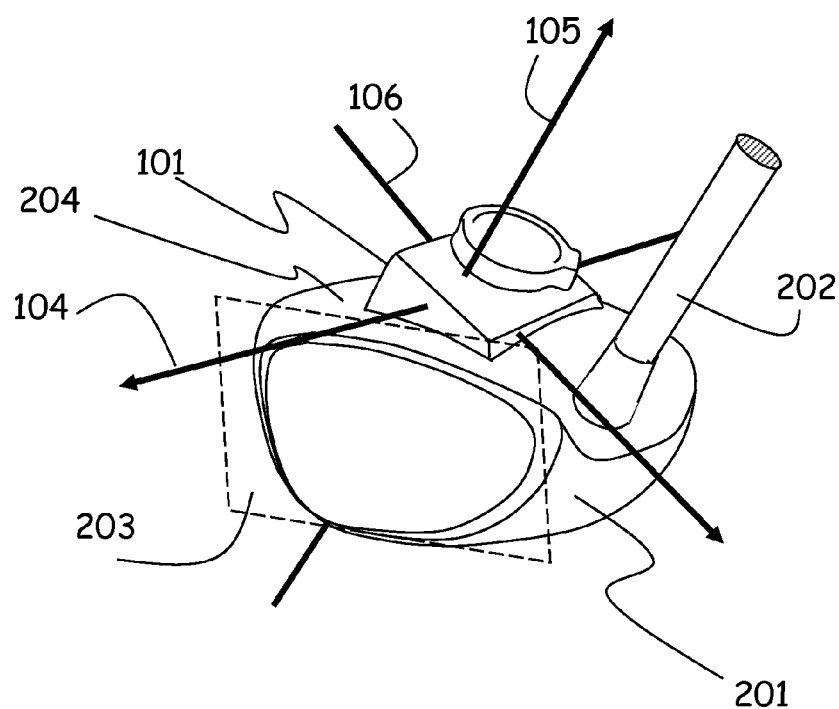
FIG. 2 is a perspective view of the club head module attached to the club head and the alignment of the club head module three orthogonal measurement axes $x_f$, $y_f$, and $z_f$, to the golf club structure.

FIG. 2 shows the preferred embodiment of the invention, which is the module 101 with three orthogonal measurement axes 104, 105 and 106 that is attached to the top surface 204 of the club head 201. The club head module 101 attachment surface 107 is attached to club head 201 top surface 204 with a conventional double sided tape with adhesive on top and bottom surfaces (not shown).

For the club head module 101 mounted perfectly on the club head 201 top surface 204 the following relations are achieved: The $z_f$-axis 105 is aligned so that it is parallel to the club shaft 202. The $x_f$-axis 104 is aligned so that is orthogonal to the $z_f$-axis 105 and perpendicular to the plane 203 that would exist if the club face has a zero loft angle. The $y_f$-axis 106 is aligned orthogonally to both the $x_f$-axis 104 and $z_f$-axis 105.

With these criteria met, the plane created by the $x_f$-axis 104 and the $y_f$-axis 106 is perpendicular to the non-flexed shaft 202. In addition the plane created by the $y_f$-axis 106 and the $z_f$-axis 105 is parallel to the plane 203 that would exist if the club face has a zero loft angle.

The mathematical label $a_{sx}$ represents the acceleration force measured by a sensor along the club head module 101 $x_f$-axis 104. The mathematical label $a_{sy}$ represents the acceleration force measured by a sensor along the club head module 101 $y_f$-axis 106. The mathematical label $a_{sz}$ represents the acceleration force measured by a sensor along the club head module 101 $z_f$-axis 105.

If the club head module of the preferred embodiment is not aligned exactly with the references of the golf club there is an algorithm that is used to detect and calculated the angle offset from the intended references of the club system and a method to calibrate and correct the measured data. This algorithm is covered in detail after the analysis is shown for proper club head module attachment with no mounting angle variations.

Figure 3:
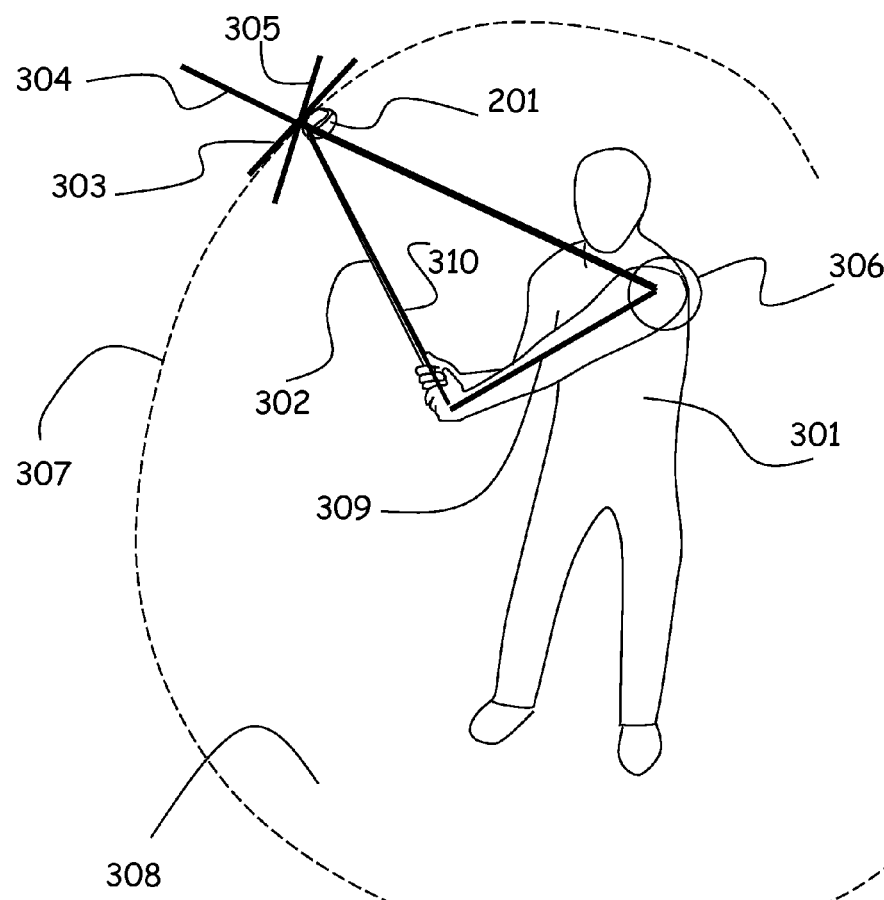
FIG. 3 is a perspective view of the "inertial" motion axes of the club head motion $x_{cm}$, $y_{cm}$ and $z_{cm}$ as the golfer swings the club and how these axes relate to the multi-lever model components of the golfer's swing.

Club head motion is much more complicated than just pure linear accelerations during the swing. It experiences angular rotations of the fixed sensor orthogonal measurement axes, $x_f$-axis 104, $y_f$-axis 106 and $z_f$-axis 105 of module 101 around all the center of mass inertial acceleration force axes during the swing, as shown in FIG. 3. As the golfer 301 swings the golf club 302 and the club head 201 travels on an arc there are inertial center of mass axes along which inertia forces act on the center of mass of the club head 201. These are the $x_{cm}$-axis 303, $y_{cm}$-axis 305 and $z_{cm}$-axis 304.

The three orthogonal measurement axes $x_f$-axis 104, $y_f$-axis 106 and $z_f$-axis 105 of module 101, along with a physics-based model of the multi-lever action of the swing of the golfer 301, are sufficient to determine the motion relative to the club head three-dimensional center of mass axes with the $x_{cm}$-axis 303, $y_{cm}$-axis 305 and $z_{cm}$-axis 304.

The mathematical label $a_z$ is defined as the acceleration along the $z_{cm}$-axis 304, the radial direction of the swing, and is the axis of the centrifugal force acting on the club head 201 during the swing from the shoulder 306 of the golfer 301. It is defined as positive in the direction away from the golfer 301. The mathematical label $a_x$ is the defined club head acceleration along the $x_{cm}$-axis 303 that is perpendicular to the $a_z$-axis and points in the direction of instantaneous club head inertia on the swing arc travel path 307. The club head acceleration is defined as positive when the club head is accelerating in the direction of club head motion and negative when the club head is decelerating in the direction of club head motion. The mathematical label $a_y$ is defined as the club head acceleration along the $y_{cm}$-axis 305 and is perpendicular to the swing plane 308.

During the golfer's 301 entire swing path 308, the dynamically changing relationship between the two coordinate systems, defined by the module 101 measurements coordinate system axes $x_f$-axis 104, $y_f$-axis 106 and $z_f$-axis 105 and the inertial motion acceleration force coordinate system axes $x_{cm}$-axis 303, $y_{cm}$-axis 305 and $z_{cm}$-axis 304, must be defined. This is done through the constraints of the multi-lever model partially consisting of the arm lever 309 and the club shaft lever 310.

Figure 4:
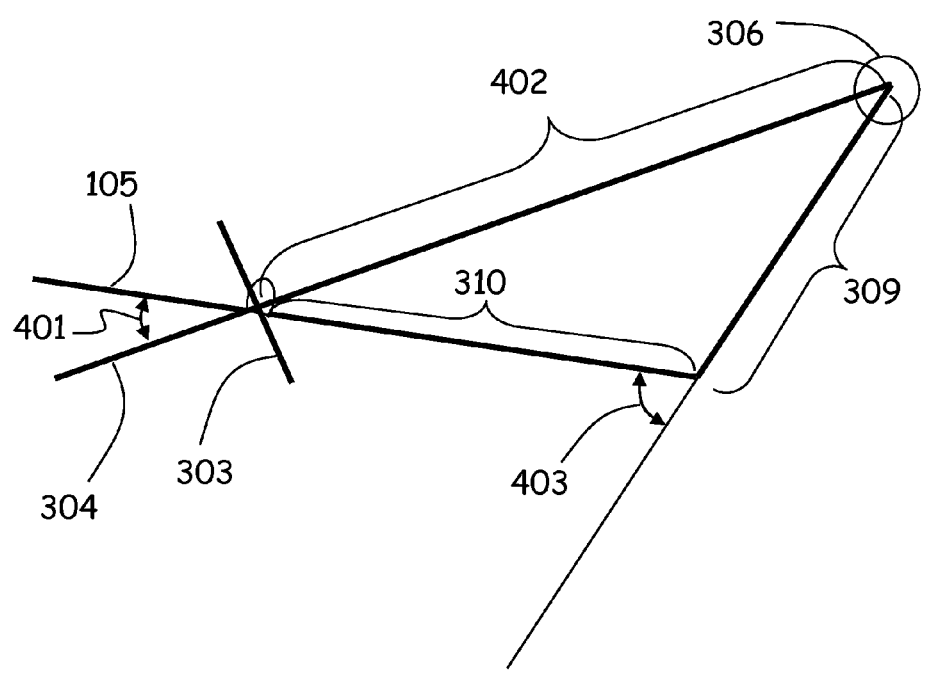
FIG. 4 shows the multi-lever variable radius model system and two key interdependent angles $\eta$ and $\alpha$ and their relationship between the two coordinate systems; the measured axes of club head module $x_f$, $y_f$ and $z_f$, and a second coordinate system comprising the inertial motion axes of club head travel $x_{cm}$, $y_{cm}$ and $z_{cm}$.

The multi lever system as shown in FIG. 4 shows two interdependent angles defined as angle $\eta$ 401 which is the angle between the club head module 101 $z_f$-axis 105 and the inertial $z_{cm}$-axis 304 and the angle $\alpha$ 403 which is the sum of wrist cock angle and shaft flex lag/lead angle (shown later in FIGS. 7 and 7A). The angle $\eta$ 401 is also the club head rotation around the $y_{cm}$-axis 106 (not shown in FIG. 4 but is perpendicular to the page at the club head center of mass) and is caused largely by the angle of wrist cock, and to a lesser extent club shaft flexing during the swing. The length of the variable swing radius R 402 is a function of the fixed length arm lever 309, the fixed length club shaft lever 310 and the angle $\eta$ 401. The angle $\eta$ 401 can vary greatly, starting at about 40 degrees or larger at the start of the downswing and approaches zero at club head maximum velocity. The inertial $x_{cm}$-axis 303 is as previously stated perpendicular to the inertial $z_{cm}$-axis 304 and variable radius R 402.

Figure 5:
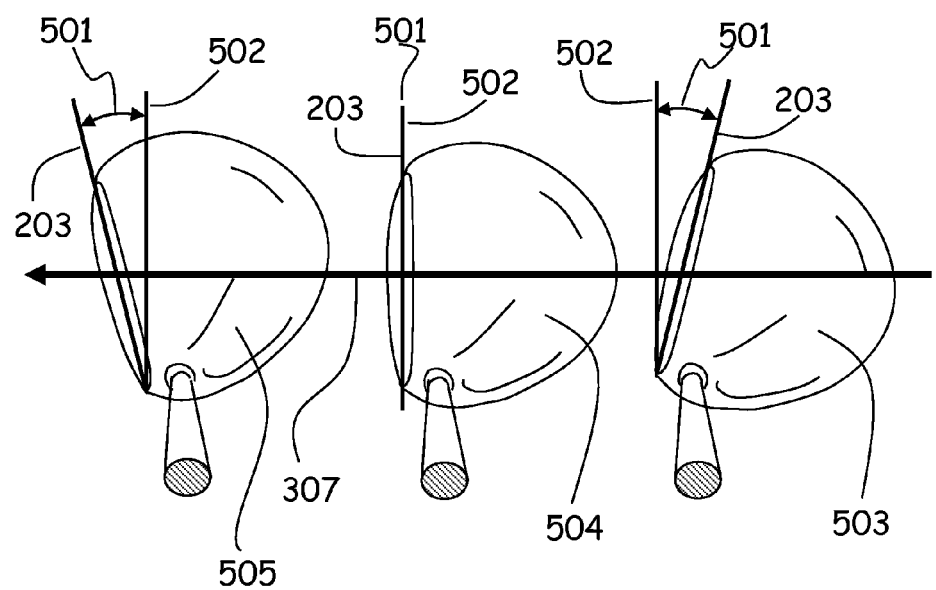
FIG. 5 shows the club face angle $\Phi$ for different club orientations referenced to the club head travel path.

FIG. 5 shows the angle $\Phi$ 501 which is the club face angle and is defined as the angle between the plane 502 that is perpendicular to the club head travel path 307 and the plane that is defined for zero club face loft 203. The angle $\Phi$ 501 also represents the club head rotation around the $z_f$-axis 105. The angle $\Phi$ 501 varies greatly throughout the swing starting at about 90 degrees or larger at the beginning of the downswing and becomes less positive and perhaps even negative by the end of the down stroke. When the angle $\Phi$ 501 is positive the club face angle is said to be "OPEN" as shown in club head orientation 503. During an ideal swing the angle Φ 501 will be zero or said to be "SQUARE" at the point of maximum club head velocity as shown in club head orientation 504. If the angle Φ 501 is negative the club face angle is said to be "CLOSED" as shown in club head orientation 505.

Figure 6:
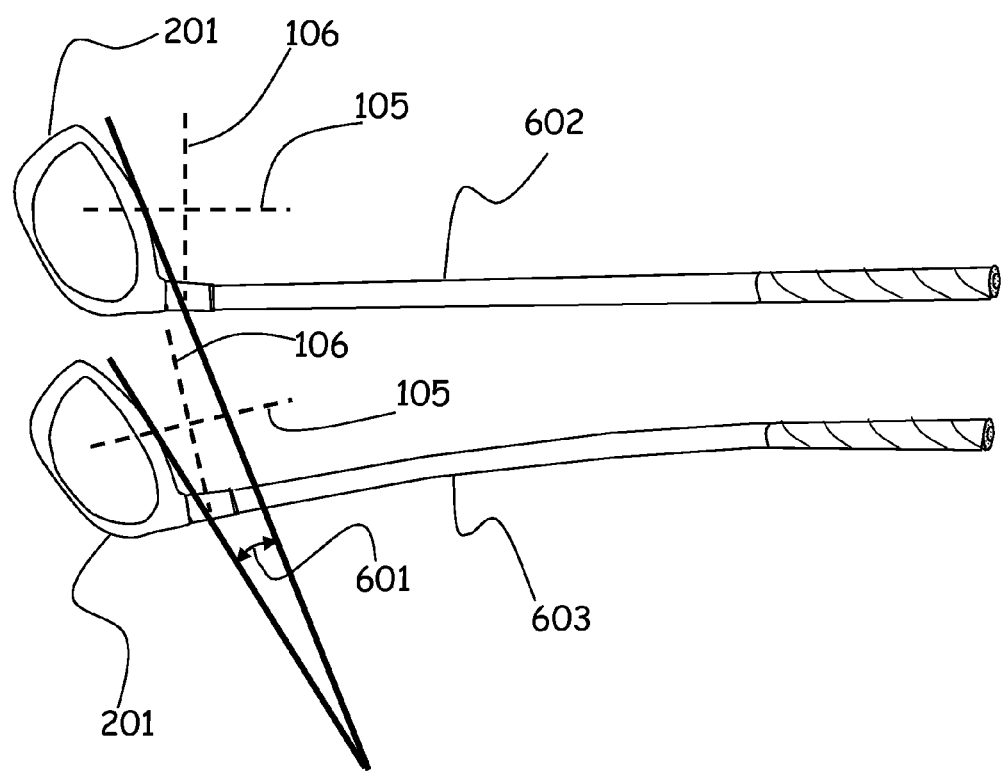
FIG. 6 shows the toe down angle, $\Omega$, and it's reference to the shaft bow state and measurement axis dynamics.

FIG. 6 shows angle Ω 601 which is referred to as the toe down angle and is defined as the angle between the top of a club head 201 of a golf club with a non bowed shaft state 602 and a golf club head 201 of a golf club with bowed shaft state 603 due to the centrifugal force pulling the club head toe downward during the swing. The angle Ω is a characteristic of the multi-lever model representing the non rigid club lever. The angle Ω 601 also represents the club head 201 rotation around the $x_f$-axis 104 (not shown in FIG. 6, but which is perpendicular to the $y_f$-axis 106 and $z_f$-axis 105 intersection). The angle Ω 601 starts off at zero at the beginning of the swing, and approaches a maximum value of a few degrees at the maximum club head velocity.

Figures 7, 7A:
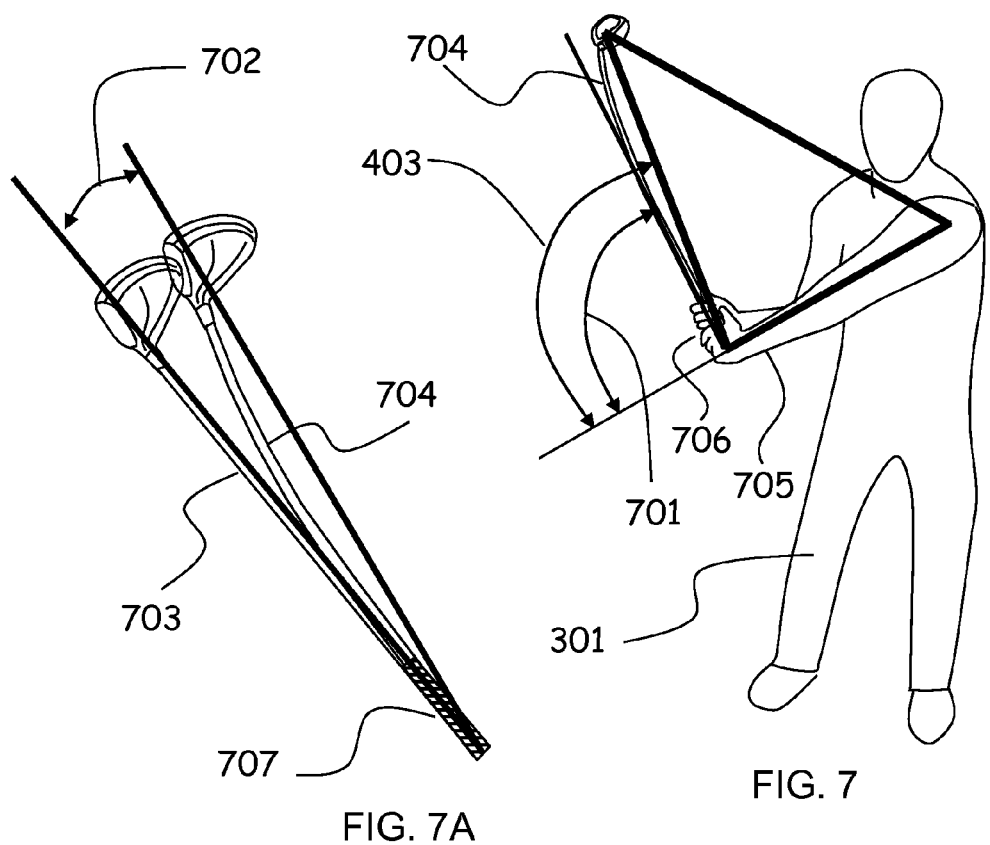
FIGS. 7 and 7A shows wrist cock angle $\alpha_{wc}$, and the shaft flex lag/lead angle $\alpha_{sf}$ which together sum to the angle $\alpha$.

FIGS. 7 and 7A show the angle α 403 which is the sum of angles $α_{wc}$ 701, defined as the wrist cock angle, and $α_{sf}$ 702, defined as the shaft flex lag/lead angle. The angle $α_{sf}$ 702 is the angle between a non-flexed shaft 703 and the flexed shaft state 704, both in the swing plane 308 defined in FIG. 3, and is one characteristic of the non rigid lever in the multi-lever model. The shaft leg/lead flex angle $α_{sf}$ 702 is caused by a combination of the inertial forces acting on the club and the wrist torque provided by the golfer's 301 wrists 705 and hands 706 on the shaft grip 707.

Figure 8:
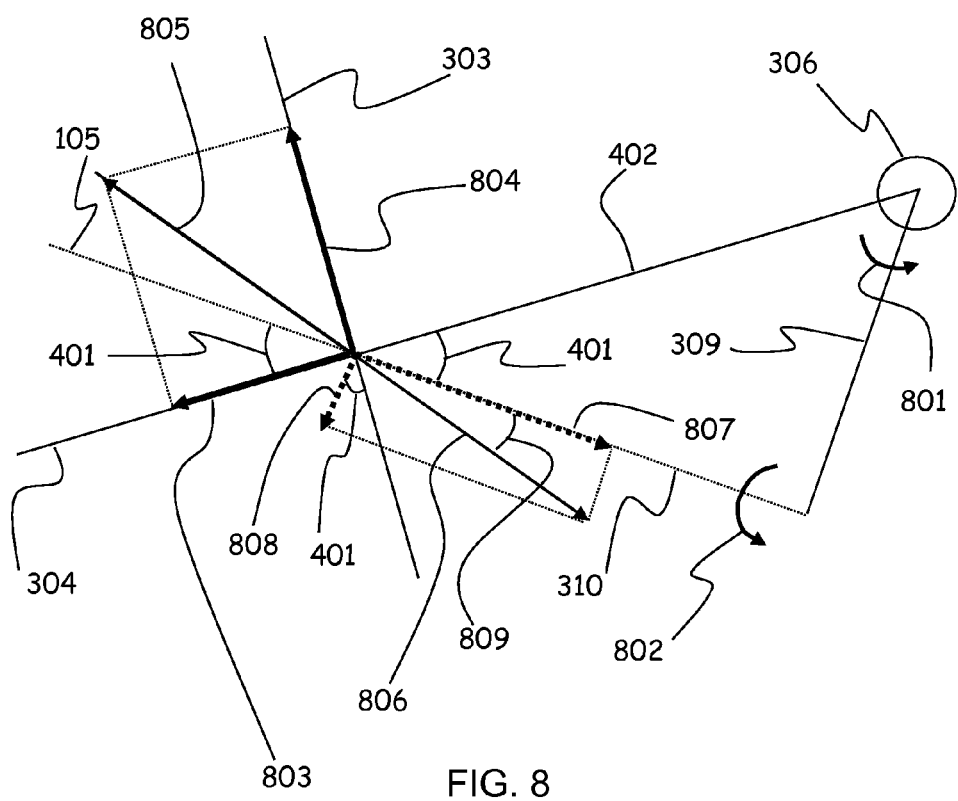
FIG. 8 shows the force balance for the multi-lever variable radius swing model system and the inter-relationship to both axes systems.

FIG. 8 shows the force balance for the multi-lever swing system. The term $a_v$ 805 is the vector sum of $a_x$ 804 and $a_z$ 803. The resulting force is given by $F_v = m_s a_v$ where $m_s$ is the mass of the club head system. The term $F_v$ 806 is also, from the force balance, the vector sum of the tensile force, $F_t$ 807, in the shaft due to the shoulder torque 801, and $F_{wt}$ 808, due to wrist torque 802. The angle between force vector $F_v$ 806 and the swing radius, R 402, is the sum of the angles η 401 and $η_{wt}$ 809.

There are several ways to treat the rotation of one axes frame relative to another, such as the use of rotation matrices. The approach described below is chosen because it is intuitive and easily understandable, but other approaches with those familiar with the art would fall under the scope of this invention.

Using the multi-lever model using levers, rigid and non-rigid, the rotation angles describing the orientation relationship between the module measured axis coordinate system and the inertial acceleration force axes coordinate system can be determined from the sensors in the club head module 101 through the following relationships:

$$a_{sx} = a_x \cos(Φ)\cos(η) - a_y \sin(Φ) - a_z \cos(Φ)\sin(η) \quad 1.$$

$$a_{sy} = a_x \sin(Φ)\cos(η) + a_y \cos(Φ) + a_z (\sin(Ω) - \sin(Φ)\sin(η)), \quad 2.$$

$$a_{sz} = a_x \sin(η) - a_y \sin(Ω)\cos(Φ) + a_z \cos(η) \quad 3.$$

The following is a reiteration of the mathematical labels for the above equations.

$a_x$ is the club head acceleration in the $x_{cm}$-axis 303 direction.

$a_y$ is the club head acceleration in the $y_{cm}$-axis 305 direction.

$a_z$ is the club head acceleration in the $z_{cm}$-axis 304 direction.

$a_{sx}$ is the acceleration value returned by the club head module 101 sensor along the $x_f$-axis 104.

$a_{sy}$ is the acceleration value returned by the club head module 101 sensor along the $y_f$-axis 106.

$a_{sz}$ is the acceleration value returned by the club head module 101 sensor along the $z_f$-axis 105.

During a normal golf swing with a flat swing plane 308, $a_y$ will be zero, allowing the equations to be simplified:

$$a_{sx} = a_x \cos(Φ)\cos(η) - a_z \cos(Φ)\sin(η) \quad 4.$$

$$a_{sy} = a_x \sin(Φ)\cos(η) + a_z (\sin(Ω) - \sin(Φ)\sin(η)) \quad 5.$$

$$a_{sz} = a_x \sin(η) + a_z \cos(η) \quad 6.$$

These equations are valid for a "free swing" where there is no contact with the golf ball.

The only known values in the above are $a_{sx}$, $a_{sy}$, and $a_{sz}$ from the three sensors. The three angles are all unknown. It will be shown below that $a_x$ and $a_z$ are related, leaving only one unknown acceleration. However, that still leaves four unknowns to solve for with only three equations. The only way to achieve a solution is through an understanding the physics of the multi-lever variable radius swing system dynamics and choosing precise points in the swing where physics governed relationships between specific variables can be used.

The angle Φ 501, also known as the club face approach angle, varies at least by 180 degrees throughout the backswing, downswing, and follow through. Ideally it is zero at maximum velocity, but a positive value will result in an "open" clubface and negative values will result in a "closed" face. The angle Φ 501 is at the control of the golfer and the resulting swing mechanics, and is not dependent on either $a_x$ or $a_z$. However, it can not be known a-priori, as it depends entirely on the initial angle of rotation around the shaft when the golfer grips the shaft handle and the angular rotational velocity of angle Φ 501 during the golfer's swing.

The angle Ω 601, on the other hand, is dependent on $a_z$, where the radial acceleration causes a centrifugal force acting on the center of mass of the club head, rotating the club head down around the $x_c$-axis into a "toe" down position of several degrees. Therefore, angle Ω 601 is a function of $a_z$. This function can be derived from a physics analysis to eliminate another unknown from the equations.

The angle η 401 results from both club shaft angle 702 lag/lead during the downswing and wrist cock angle 701. Wrist cock angle is due both to the mechanics and geometry relationships of the multi lever swing model as shown in FIG. 4 and the amount of torque exerted by the wrists and hands on the shaft.

Before examining the specifics of these angles, it is worth looking at the general behavior of equations (4) through (6). If both angle Ω 601 and angle η 401 were always zero, which is equivalent to the model used by Hammond in U.S. Pat. No. 3,945,646, the swing mechanics reduces to a single lever constant radius model. For this case:

$$a_{sx} = a_x \cos(Φ) \quad 7.$$

$$a_{sy} = a_x \sin(Φ) \quad 8.$$

$$a_{sz} = a_z \quad 9.$$

This has the simple solution for club face angle Φ of:

$$10. \quad \tan(Φ) = \frac{a_{sy}}{a_{sx}}$$

In Hammond's U.S. Pat. No. 3,945,646 he states in column 4 starting in line 10 "By computing the vector angle from the acceleration measured by accelerometers 12 and 13, the position of the club face 11 at any instant in time during the swing can be determined." As a result of Hammond using a single lever constant radius model which results in equation 10 above, it is obvious he failed to contemplate effects of the centrifugal force components on sensor 12 and sensor 13 of his patent. The large error effects of this can be understood by the fact that the $a_z$ centrifugal acceleration force is typically 50 times or more greater than the measured acceleration forces of $a_{sx}$ and $a_{sy}$ for the last third of the down swing and first third of the follow through. Therefore, even a small angle $\Omega$ 601 causing an $a_z$ component to be rotated onto the measured $a_{sy}$ creates enormous errors in the single lever golf swing model.

In addition, the effect of the angle $\eta$ 401 in the multi lever variable radius swing model is to introduce $a_z$ components into $a_{sx}$ and $a_{sy}$, and an $a_x$ component into $a_{sz}$. The angle $\eta$ 401 can vary from a large value at the start and midpoint of the down stroke when $a_z$ is growing from zero. In later portion of the down stroke $a_z$ becomes very large as angle $\eta$ 401 tends towards zero at maximum velocity. Also, as mentioned above, the angle $\eta$ 401 introduces an $a_x$ component into $a_{sz}$. This component will be negligible at the point of maximum club head velocity where angle $\eta$ 401 approaches zero, but will be significant in the earlier part of the swing where angle $\eta$ 401 is large and the value of $a_x$ is larger than that for $a_z$.

The $\cos(\eta)$ term in equations (4) and (5) is the projection of $a_x$ onto the $x_f$-$y_f$ plane, which is then projected onto the $x_f$-axis 104 and the $y_f$ axis 106. These projections result in the $a_x \cos(\Phi)\cos(\eta)$ and $a_x \sin(\Phi)\cos(\eta)$ terms respectively in equations (4) and (5). The projection of $a_x$ onto the $z_f$-axis 105 is given by the $a_x \sin(\eta)$ term in equation (6).

The $\sin(\eta)$ terms in equations (4) and (5) are the projection of $a_z$ onto the plane defined by $x_f$-axis 104 and the $y_f$-axis 106, which is then projected onto the $x_f$-axis 104 and $y_f$-axis 106 through the $a_z \cos(\Phi)\sin(\eta)$ and $a_z \sin(\Phi)\sin(\eta)$ terms respectively in equations (4) and (5). The projection of $a_z$ onto the $z_f$-axis 105 is given by the $a_z \cos(\eta)$ term in equation (6).

The angle $\Omega$ 601 introduces yet another component of $a_z$ into $a_{sy}$. The angle $\Omega$ 601 reaches a maximum value of only a few degrees at the point of maximum club head velocity, so its main contribution will be at this point in the swing. Since angle $\Omega$ 601 is around the $x_f$-axis 104, it makes no contribution to $a_{sx}$, so its main effect is the $a_z \sin(\Omega)$ projection onto the $y_f$-axis 106 of equation (5). Equations (4) and (5) can be simplified by re-writing as:

11. $a_{sx} = (a_x \cos(\eta) - a_z \sin(\eta))\cos(\Phi) = f(\eta)\cos(\Phi)$ and 12. $a_{sy} = (a_x \cos(\eta) - a_z \sin(\eta))\sin(\Phi) + a_z \sin(\Omega)$
$= f(\eta)\sin(\Phi) + a_z \sin(\Omega)$ where 13. $f(\eta) = a_x \cos(\eta) - a_z \sin(\eta)$.

From (11):

14. $f(\eta) = \dfrac{a_{sx}}{\cos(\Phi)}$ which when inserted into (12) obtains:

15. $a_{sy} = a_{sx} \tan(\Phi) + a_z \sin(\Omega)$

From equation (15) it is seen that the simple relationship between $a_{sx}$ and $a_{sy}$ of equation (10) is modified by the addition of the $a_z$ term above. Equations (4) and (6) are re-written as:

16. $a_x = \dfrac{a_{sx}}{\cos(\eta)\cos(\Phi)} + \dfrac{a_z \sin(\eta)}{\cos(\eta)}$ 17. $a_z = \dfrac{a_{sz}}{\cos(\eta)} - \dfrac{a_x \sin(\eta)}{\cos(\eta)}$.

These equations are simply solved by substitution to yield:

18. $a_z = a_{sz}\cos(\eta) - a_{sx}\dfrac{\sin(\eta)}{\cos(\Phi)}$.

19. $a_x = a_{sz}\sin(\eta) + a_{sx}\dfrac{\cos(\eta)}{\cos(\Phi)}$.

Equation (19) can be used to find an equation for $\sin(\eta)$ by re-arranging, squaring both sides, and using the identity, $\cos^2(\eta) = 1 - \sin^2(\eta)$, to yield a quadratic equation for $\sin(\eta)$, with the solution:

20. $\sin(\eta) = \dfrac{a_x a_{sz} + \dfrac{a_{sx}^2}{\cos^2(\Phi)}\sqrt{1 - \cos^2(\Phi)\left(\dfrac{a_{sz}^2 - a_x^2}{a_{sx}^2}\right)}}{a_{sz}^2 + \dfrac{a_{sx}^2}{\cos^2(\Phi)}}$.

To get any further for a solution of the three angles, it is necessary to examine the physical cause of each. As discussed above the angle $\eta$ 401 can be found from an analysis of the angle $\alpha$ 403, which is the sum of the angles $\alpha_{wc}$ 701, due to wrist cock and $\alpha_{sf}$ 702 due to shaft flex lag or lead.

Angle $\alpha$ 403, and angle $\eta$ 401 are shown in FIG. 4 in relationship to variable swing radius R 402, fixed length arm lever A 309, and fixed length club shaft lever C 310. The mathematical equations relating these geometric components are:

$R^2 = A^2 + C^2 + 2AC \cos(\alpha)$      21.

$A^2 = R^2 + C^2 - 2RC \cos(\eta)$      22.

Using $R^2$ from equation (21) in (22) yields a simple relationship between $\alpha$ and $\eta$:

$\alpha = \cos^{-1}((R\cos(\eta) - C)/A)$      23.

The swing radius, R 402, can be expressed either in terms of $\cos(\alpha)$ or $\cos(\eta)$. Equation (21) provides R directly to be:

$R = \sqrt{C^2 + A^2 + 2AC\cos(\alpha)}$.      24.

Equation (22) is a quadratic for R which is solved to be:

$R = C\cos(\eta) + \sqrt{C^2(\cos(\eta) - 1) + A^2}$.      25.

Both $\alpha$ 403 and $\eta$ 401 tend to zero at maximum velocity, for which $R_m = A + C$.

The solutions for the accelerations experienced by the club head as it travels with increasing velocity on this swing arc defined by equation (25) are:

26. $a_z = \dfrac{V_r^2}{R} - \dfrac{dV_R}{dt}$

-continued $$27.\ a_x = \frac{2}{R}V_R V_\Gamma + R\frac{d}{dt}\left(\frac{V_\Gamma}{R}\right)$$

The acceleration $a_z$ is parallel with the direction of R 402, and $a_x$ is perpendicular to it in the swing plane 308. The term $V_\Gamma$ is the velocity perpendicular to R 402 in the swing plane 308, where $\Gamma$ is the swing angle measured with respect to the value zero at maximum velocity. The term $V_R$ is the velocity along the direction of R 402 and is given by dR/dt. The swing geometry makes it reasonably straightforward to solve for both $V_R$ and its time derivative, and it will be shown that $a_z$ can also be solved for which then allows a solution for $V_\Gamma$:

$$28.\ V_\Gamma = \sqrt{Ra_z + R\frac{dV_r}{dt}}$$

Now define:

$$29.\ a_{z-radial} = \frac{V_\Gamma^2}{R}$$

so that:

$$30.\ V_\Gamma = \sqrt{Ra_{z-radial}},$$

Next define:

$$31.\ a_{ch} = \frac{dV_\Gamma(t)}{dt} = \frac{\Delta V_\Gamma(t)}{\Delta t},$$

Because (31) has the variable R 402 included as part of the time derivative equation (27) can be written:

$$32.\ a_x = a_{ch} + \frac{2}{R}V_R V_\Gamma$$

Also equation (26) can be written:

$$33.\ a_z = a_{z-radial} - \frac{dV_R}{dt}$$

The acceleration $a_v$ 805 is the vector sum of $a_x$ 804 and $a_z$ 803 with magnitude:

$$34.\ a_v = \sqrt{a_x^2 + a_z^2} = \frac{a_x}{\sin(\beta)} = \frac{a_z}{\cos(\beta)}$$

where $$35.\ \beta = \tan^{-1}\left(\frac{a_x}{a_z}\right)$$

The resulting magnitude of the force acting on the club head is then:

$$F_v = m_s a_v \quad\quad 36.$$

FIG. 8 shows this force balance for $F_v$ 806. If there is no force $F_{wt}$ 808 acting on the golf club head due to torque 802 provided by the wrists, then $F_v$ 806 is just $F_t$ 807 along the direction of the shaft, and is due entirely by the arms pulling on the shaft due to shoulder torque 801. For this case it is seen that:

$$\beta = \eta \text{ for no wrist torque.} \quad\quad 37.$$

On the other hand, when force $F_{wt}$ 808 is applied due to wrist torque 802:

$$\beta = \eta + \eta_{wt} \text{ where:} \quad\quad 38.$$

$$F_{wt} = F_v \sin(\eta_{wt}). \quad\quad 39.$$

The angle $\eta_{wt}$ 809 is due to wrist torque 802. From (38):

$$40.\ \eta = \left(1 - \frac{\eta_{wt}}{\beta}\right)\beta = C_\eta \beta$$

where $C_\eta < 1$ is a curve fitting parameter to match the data, and is nominally around the range of 0.75 to 0.85. From the fitted value:

$$\eta_{wt} = (1 - C_\eta)\beta \quad\quad 41.$$

Using (41) in (39) determines the force $F_{wt}$ 808 due to wrist torque 802.

Figure 9:
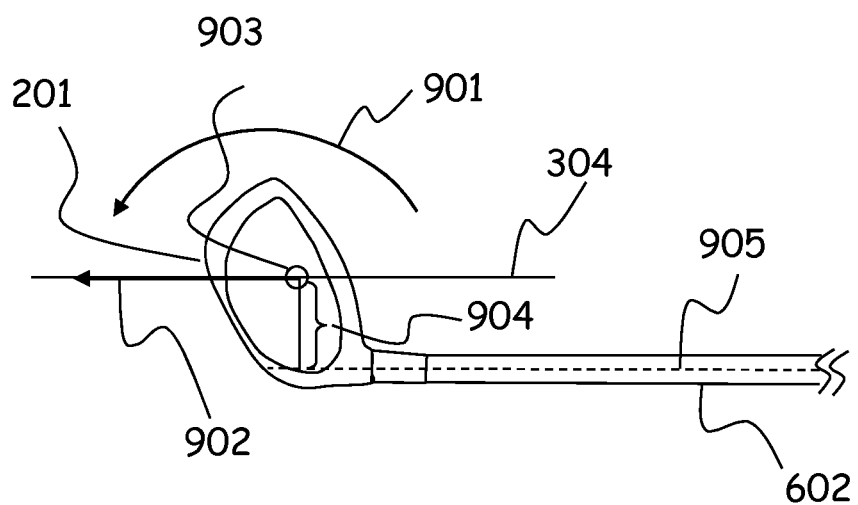
FIG. 9 shows the force balance for the flexible lever portion of the multi-lever model for the toe down angle $\Omega$.

To solve for angle $\Omega$ 601 as previously defined in FIG. 6 the force balance shown in FIG. 9 is applied to accurately determine the toe down angle $\Omega$ 601. A torque 901 acting on club head 201 with mass M is generated by the acceleration vector 902 on the $z_{cm}$-axis 304 with magnitude $a_z$ acting through the club head 201 center of mass 903. The center of mass 903 is a distance 904 from the center axis 905 of club shaft 202 with length C 310 and stiffness constant K. The mathematical label for distance 904 is d. Solving the force balance with the constraints of a flexible shaft K gives an expression for $\Omega$ 601:

$$42.\ \Omega = \frac{dC_\Omega}{C}\left(\frac{\frac{Ma_z}{KC}}{1 + \frac{Ma_z}{KC}}\right)$$

It is worth noting that from equation (42) for increasing values of $a_z$ there is a maximum angle $\Omega$ 601 that can be achieved of d $C_\Omega$/C which for a typical large head driver is around 4 degrees. The term $C_\Omega$ is a curve fit parameter to account for variable shaft stiffness profiles for a given K. In other words different shafts can have an overall stiffness constant that is equal, however, the segmented stiffness profile of the shaft can vary along the taper of the shaft.

An equation for angle $\Phi$ 501 in terms of angle $\Omega$ 601 can now be found. This is done by first using equation (17) for $a_z$ in equation (15):

$$43.\ a_{sy} = a_{sx}\frac{\sin(\Phi)}{\cos(\Phi)} + a_{sz}\cos(\eta)\sin(\Omega) - a_{sx}\frac{\sin(\eta)\sin(\Omega)}{\cos(\Phi)}$$

Re-arranging terms:

$$(a_{sy} - a_{sz}\cos(\eta)\sin(\Omega))\cos(\Phi) = a_{sx}\sin(\Phi) - a_{sx}\sin(\eta)\sin(\Omega) \quad\quad 44.$$

Squaring both sides, and using the identity $\cos^2(\Phi) = 1 - \sin^2(\Phi)$ yields a quadratic equation for $\sin(\Phi)$:

$$\sin^2(\Phi)[a_{sx}^2 + (a_{sy} - a_{sz}\cos(\eta)\sin(\Omega))^2] - 2a_{sx}^2\sin(\Phi)\sin(\eta)\sin(\Omega) + a_{sx}^2(\sin(\eta)\sin(\Omega))^2 - (a_{sy} - a_{sz}\cos(\eta)\sin(\Omega))^2 = 0 \quad\quad 45.$$

Equation (45) has the solution:

$$46.\ \sin(\Phi) = \frac{1}{2b_1}\left[-b_2 + \sqrt{b_2^2 - 4b_1 b_3}\right]$$

where the terms in (46) are:

$$b_1 = a_{sx}^2 + (a_{sy} - a_{sz}\cos(\eta)\sin(\Omega))^2$$

$$b_2 = -2a_{sx}^2 \sin(\eta)\sin(\Omega)$$

$$b_3 = a_{sx}^2(\sin(\eta)\sin(\Omega))^2 - (a_{sy} - a_{sz}\cos(\eta)\sin(\Omega))^2$$

Equations (42) for $\Omega$ 601, (46) for $\Phi$ 501, and (20) for $\eta$ 401 need to be solved either numerically or iteratively using equations (32) for $a_x$, (33) for $a_z$, and (25) for R 402. This task is extremely complex. However, some innovative approximations can yield excellent results with much reduced complexity. One such approach is to look at the end of the power-stroke segment of the swing where $V_R$ and its time derivative go to zero, for which from equations (32), (33), (35) and (40):

$$47.\ \eta = C_\eta \tan^{-1}\left(\frac{a_{ch}}{a_{z\text{-}radial}}\right)$$

In this part of the swing the $a_{sx}$ term will be much smaller than the $a_{sz}$ term and equation (18) can be approximated by:

$$a_z = a_{z\text{-}radial} = a_{sz}\cos(\eta). \qquad 48.$$

During the earlier part of the swing, the curve fit coefficient $C_\eta$ would accommodate non-zero values of $V_R$ and its time derivative as well as the force due to wrist torque 802.

The maximum value of $\eta$ 401 is nominally around 40 degrees for which from (48) $a_{ch}/a_{z\text{-}radial}=1.34$ with $C_\eta=0.75$. So equation (47) is valid for the range from $a_{ch}=0$ to $a_{ch}=1.34$ $a_{z\text{-}radial}$, which is about a third of the way into the down-stroke portion of the swing. At the maximum value of $\eta$ 401 the vector $a_v$ 805 is 13 degrees, or 0.23 radians, off alignment with the $z_f$ axis and its projection onto the $z_f$ axis 105 is $a_{sz} = a_v \cos(0.23) = 0.97 a_v$. Therefore, this results in a maximum error for the expression (48) for $a_z = a_{z\text{-}radial}$ of only 3%. This amount of error is the result of ignoring the $a_{sx}$ term in equation (18). This physically means that for $a_z$ in this part of the swing the $a_{z\text{-}radial}$ component value dominates that of the $a_{sx}$ component value. Equation (47) can not be blindly applied without first considering the implications for the function $f(\eta)$ defined by equations (13) and (14), which has a functional dependence on $\cos(i)$ through the $a_{sx}$ term, which will not be present when (47) is used in (13). Therefore, this $\cos(\Phi)$ dependence must be explicitly included when using (47) to calculate (13) in equation (12) for $a_{sy}$, resulting in:

$$a_{sy} = (a_x\cos(\eta) - a_z\sin(\eta))\tan(\Phi) + a_z\sin(\Omega). \qquad 49.$$

Equation (49) is applicable only when equation (47) is used for the angle $\eta$ 401.

A preferred embodiment is next described that uses the simplifying equations of (47) through (49) to extract results for $\Phi$ 501 and $\eta$ 401 using (42) as a model for $\Omega$ 601. It also demonstrates how the wrist cock angle $\alpha_{wc}$ 701 and shaft flex angle $\alpha_{sf}$ 702 can be extracted, as well as the mounting angle errors of the accelerometer module. Although this is the preferred approach, other approaches fall under the scope of this invention.

The starting point is re-writing the equations in the following form using the approximations $a_z = a_{z\text{-}radial}$ and $a_x = a_{ch}$. As discussed above these are excellent approximations in the later part of the swing. Re-writing the equations (4) and (49) with these terms yields:

$$a_{sx} = a_{ch}\cos(\Phi)\cos(\eta) - a_{z\text{-}radial}\cos(\Phi)\sin(\eta) \qquad 50.$$

$$a_{sy} = a_{ch}\tan(\Phi)\cos(\eta) + a_{z\text{-}radial}\sin(\Omega) - a_{z\text{-}radial}\tan(\Phi)\sin(\eta) \qquad 51.$$

$$a_{z\text{-}radial} = a_{sz}\cos(\eta) \qquad 52.$$

Simplifying equation (31):

$$53.\ a_{ch} = \frac{dV}{dt}$$

In this approximation $V = V_\Gamma$ is the club head velocity and dt is the time increment between sensor data points. The instantaneous velocity of the club head traveling on an arc with radius R is from equation (29):

$$54.\ V = \sqrt{a_{z\text{-}radial} R} = a_{z\text{-}radial}^{1/2} R^{1/2}$$

for which:

$$55.\ a_{ch} = \frac{dV}{dt} = \frac{1}{2}\left(\frac{1}{R}\frac{dR}{dt} + \frac{1}{a_{z\text{-}radial}}\frac{da_{z\text{-}radial}}{dt}\right)\sqrt{R a_{z\text{-}radial}}$$

Using equation (52) for $a_{z\text{-}radial}$ in (55):

$$56.\ a_{ch} = \frac{1}{2}\left(\frac{1}{R}\frac{dR}{dt} + \frac{1}{a_{sz}}\frac{da_{sz}}{dt} - \tan(\eta)\frac{d\eta}{dt}\right)\sqrt{R a_{sz}\cos(\eta)}$$

During the early part of the downswing, all the derivative terms will contribute to $a_{ch}$, but in the later part of the downswing when R is reaching its maximum value, $R_{max}$, and $\eta$ is approaching zero, the dominant term by far is the $da_{sz}/dt$ term, which allows the simplification for this part of the swing:

$$57.\ a_{ch} = \frac{1}{2}\left(\frac{1}{a_{sz}}\frac{da_{sz}}{dt}\right)\sqrt{R a_{sz}\cos(\eta)}$$

With discreet sensor data taken at time intervals $\Delta t$, the equivalent of the above is:

$$58.\ a_{ch} = \frac{\sqrt{R\cos(\eta)}}{\Delta t}\left(\sqrt{a_{sz}(t_n)} - \sqrt{a_{sz}(t_{n-1})}\right)$$

It is convenient to define the behavior for $a_{ch}$ for the case where $R = R_{max}$ and $\eta = 0$, so that from equation (52) $a_{z\text{-}radial} = a_{sz}$, which defines:

$$59.\ a_{chsz} = \frac{\sqrt{R_{max}}}{\Delta t}\left(\sqrt{a_{sz}(t_n)} - \sqrt{a_{sz}(t_{n-1})}\right)$$

Then the inertial spatial translation acceleration component of the club head is:

$$60.\ a_{ch} = a_{chsz} \frac{\sqrt{R\cos(\eta)}}{\sqrt{R_{max}}}$$

Substituting equation (52) and (60) back into equations (50) and (51) we have the equations containing all golf swing metric angles assuming no module mounting angle errors in terms of direct measured sensor outputs:

$$a_{sx}=a_{chsz}(\sqrt{R\cos(\eta)}/\sqrt{R_{Max}})\cos(\Phi)\cos(\eta)-a_{sz}\cos(\eta)\cos(\Phi)\sin(\eta) \quad 61.$$

$$a_{sy}=a_{chsz}(\sqrt{R\cos(\eta)}/\sqrt{R_{max}})\tan(\Phi)\cos(\eta)+a_{sz}\cos(\eta)\sin(\Omega)-a_{sz}\cos(\eta)\tan(\Phi)\sin(\eta) \quad 62.$$

Using equation (62) to solve for $\Phi$, since this is the only equation that contains both $\eta$ and $\Omega$, yields:

$$63.\ \tan(\Phi) = \frac{a_{sy} - a_{sz}\cos(\eta)\sin(\Omega)}{a_{chsz}\left(\sqrt{R\cos(\eta)}/\sqrt{R_{Max}}\right)\cos(\eta) - a_{sz}\cos(\eta)\sin(\eta)}$$

Now there are two equations with three unknowns. However, one of the unknowns, $\eta$, has the curve fit parameter $C_\eta$ that can be iteratively determined to give best results for continuity of the resulting time varying curves for each of the system variables. Also, there are boundary conditions from the multi-lever model of the swing that are applied, to specifics points and areas of the golf swing, such as the point of maximum club head velocity at the end of the downstroke, where:

1. For a golf swing approaching max velocity the value of $\eta$ approaches zero,
2. $\Omega$ is at a maximum value when centrifugal force is highest, which occurs at maximum velocity.
3. The club face angle, $\Phi$, can vary greatly at maximum club head velocity. However, regardless of the angle at maximum velocity the angle is changing at a virtual constant rate just before and after the point of maximum club head velocity. This knowledge allows for all equations to be solved, through an interactive process using starting points for the curve fit parameters.

The angle $\Omega$ 601 is a function of $a_{sz}$ through equations (42), (48) and (52). The curve fit constant, $C_\Omega$, is required since different shafts can have an overall stiffness constant that is equal, however, the segmented stiffness profile of the shaft can vary along the taper of the shaft. The value of $C_\Omega$ will be very close to one, typically less than 1/10 of a percent variation for the condition of no module mounting angle error from the intended alignment. Values of $C_\Omega$ greater or less than 1/10 of a percent indicates a module mounting error angle along the $y_{cm}$-axis which will be discussed later. Rewriting equation (42) using (52):

$$64.\ \Omega = \frac{C_\Omega d m_s a_{sz}\cos(\eta)}{C(KC + m_s a_{sz}\cos(\eta))}$$

The constants in equation (64) are:
  $C_\Omega$ Multiplying curve fit factor applied for iterative solution
  d Distance from housel to center of gravity (COG) of club head
  $m_s$ mass of club head system, including club head and Club Head Module
  $a_{sz}$ The measured $z_f$-axis 105 acceleration force value
  K Stiffness coefficient of shaft supplied by the golfer or which can Be determined in the calibration process associated with the user profile entry section of the analysis program
  C Club length The angle $\eta$ 401 is found from equation (47):

$$65.\ \eta = C_\eta \tan^{-1}\left(\frac{a_{ch}}{a_{z\text{-}radial}}\right)$$

The curve fit parameter, $C_\eta$, has an initial value of 0.75.

An iterative solution process is used to solve equations (61), (63), and (64), using (65) for $\eta$ 401, which has the following defined steps for the discreet data tables obtained by the sensors:

1. Determine from sample points of $a_{sz}$ the zero crossing position of $a_{chsz}$. This is the point where the club head acceleration is zero and therefore the maximum velocity is achieved. Because the samples are digitized quantities at discrete time increments there will be two sample points, where $a_{chsz}$ has a positive value and an adjacent sample point where $a_{chsz}$ has a negative value.
2. Course tune of $\Omega$ 601: Use initial approximation values to solve for the numerator of $\tan(\Phi)$ of equation (63) with respect to the sample point where $a_{ch}$ passes through zero:
    a. Numerator of $\tan(\Phi) = \{a_{sy} - a_{sz}\cos(\eta)\sin(\Omega)\}$
    b. The numerator of $\tan(\Phi)$ in equation 63 represents the measured value of $a_{sy}$ minus $a_{z\text{-}radial}$ components resulting from angle $\Omega$ with the following conditions at maximum velocity:
    i. Toe down angle $\Omega$, which is at its maximum value at maximum club head velocity, where maximum $a_{sz}$ is achieved at $\eta=0$, for which $a_{sz}=a_{z\text{-}radial}$ From equation (52).
    ii. Angle $\eta$ 401, which is a function of wrist cock and shaft flex lag/lead, is zero when maximum velocity is reached and $a_{ch}$ is zero.
    c. Use the multiplying constant $C_\Omega$ to adjust the $\Omega$ 601 equation so that the $\tan(\Phi)$ numerator function sample point value, equivalent to the first negative sample point value of $a_{ch}$, is set to the value zero.
3. Use new course tune value for the $\Omega$ 601 function to calculate $\Phi$ 501 from equation (63) for all sample points.
4. Next, fine tune the multiplying constant $C_\Omega$ of the $\Omega$ 601 function by evaluating the slope of $\Phi$ 501, for the point pairs before, through, and after maximum velocity.
    a. Examine sample point pairs of the total $\tan(\Phi)$ function given by equation (63) before maximum velocity, through maximum velocity, and after maximum velocity, evaluating slope variation across sample pairs.
    b. Evaluate sequential slope point pairs comparing slopes to determine a variation metric.
    c. Tune multiplying constant $C_\Omega$ of $\Omega$ 601 function in very small increments until the slope of $\Phi$ 501 of all sample point pairs are equivalent.
    d. Now the value of the $\Omega$ function is defined but the value of $\eta$ is still given with the initial value of $C_\eta=0.75$. Therefore, even though the value of $\Phi$ 501 is exact for values very near max velocity where $\eta$ 401 approaches zero, values of $\Phi$ 501 are only approximations away from maximum velocity since $\Phi$ 501 is a function of $\eta$ 401, which at this point is limited by the initial approximation.

5. Calculate all sample points for the for the following functions:
   a. The fine tuned function $\Omega$ 601
   b. Approximate function $\eta$ 401 with $C_\eta=0.75$.
   c. Function $\Phi$ 501 from equation (63)
   i. Which will be exact for sample points close to maximum velocity
   ii. Which will be an approximation for the sample points away from max velocity because the function $\eta$ 401 is still an approximate function.
6. Tune the multiplying curve fit constant $C_\eta$ of the $\eta$ 401 function using equation (61). This is done by rewriting equation (61) into a form which allows the comparison of $a_{sx}$ minus the $a_{sz}$ components which must be equal to $a_{chsz}$. The evaluation equation is from (61):
   a. ....

$$\{a_{sx}+a_{sz}\cos(\eta)\cos(\phi)\sin(\eta)\}/\{\cos(\phi)\cos(\eta)\}=a_{chsz}(\sqrt{R\cos(\eta)}/\sqrt{R_{Max}})$$

b. If everything were exact, the two sides of this equation would be equal. If not, they will differ by the variance:

$$\text{Variance}=\{a_{sx}+a_{sz}\cos(\eta)\cos(\phi)\sin(\eta)\}/\{\cos(\phi)\cos(\eta)\}-a_{chsz}(\sqrt{R\cos(\eta)}/\sqrt{R_{Max}})$$

c. This variance metric is summed across a significant number of sample points before and after maximum velocity for each small increment that $C_\eta$ is adjusted.
   d. The minimum summed variance metric set defines the value of the constant $C_\eta$ for the $\eta$ 401 function.
7. Compare the value of $C_\eta$ obtained at the conclusion of the above sequence with the starting value of $C_\eta$, and if the difference is greater than 0.1 repeat steps 3 through 7 where the initial value for $C_\eta$ in step 3 is the last iterated value from step 6.d. When the difference is less than 0.1, the final value of $C_\eta$ has been obtained.
8. Angle $\alpha$ 403 is now solved from equation (23) with $\eta$ 401 across all sample points:

$$\alpha=\cos^{-1}((R\cos(\eta)-C)/A)$$

a. $\alpha$ 403 represents the sum of wrist cock angle and shaft flex lag/lead angle as defined by $\alpha=\alpha_{wc}+\alpha_{sf}$.
   b. In a standard golf swing the wrist cock angle is a decreasing angle at a constant rate during the down stroke to maximum club head velocity. Therefore, the angle can be approximated as a straight line from the point where wrist cock unwind is initiated.
   c. The slope of the angle $\alpha_{wc}$ 701 is:
   i. [$\alpha_{wc}$ (at wrist cock unwind initiation)-$\alpha_{wc}$ (club head maxVelocity)]/$\Delta T$, where $\Delta T$ is the time duration for this occurrence.
   d. Since $\alpha_{wc}$ 701 goes to zero at the point of maximum velocity and the time duration $\Delta T$ is known, the function of angle $\alpha_{wc}$ 701 is now defined.
9. The shaft flex angle $\alpha_{sf}$ 702 is now defined as $\alpha_{sf}=\alpha-\alpha_{wc}$ for all sample points during down stroke. Any deviation from the straight line function of $\alpha_{wc}$ 701 is due to shaft flex.

The iterative analysis solution described above is based on the club head module being mounted so that the $x_f$-axis 104, $y_f$-axis 106, and $z_f$-axis 105 associated with the club head module 101 are aligned correctly with the golf club structural alignment elements as previously described in FIG. 2.

Since the module 101 attaches to the top of the club head 201, which is a non-symmetric complex domed surface, the mounting of the club head module 101 is prone to variation in alignment of the $x_f$-axis 104, $z_f$-axis 105, and $y_f$-axis 106 with respect to the golf club reference structures described in FIG. 2.

Figure 10:
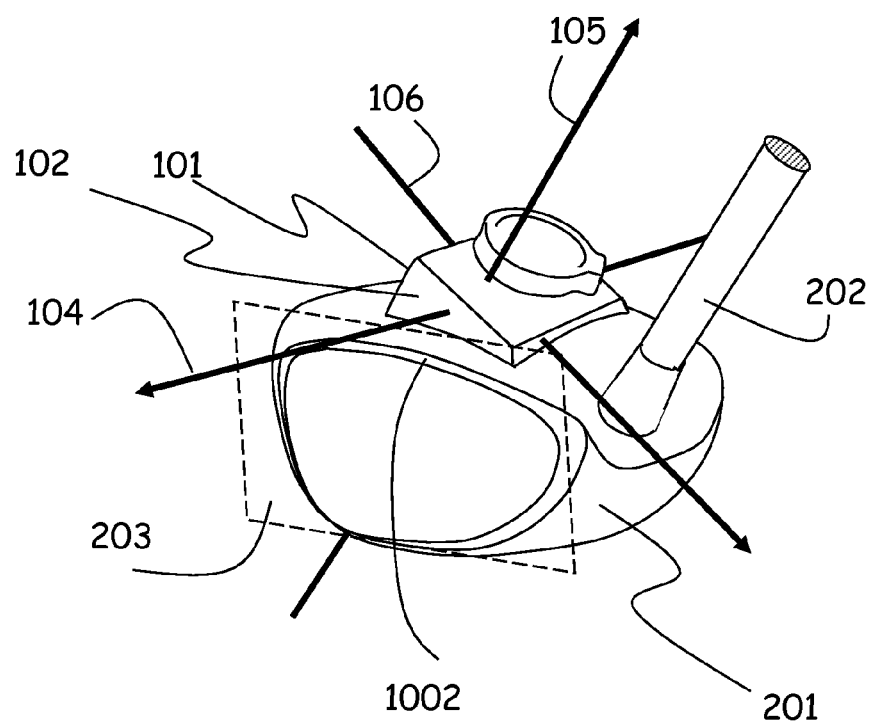
FIG. 10 shows the mounting and alignment process of the club head module being attached to the club head and the available visual alignment structure.
Figure 11:
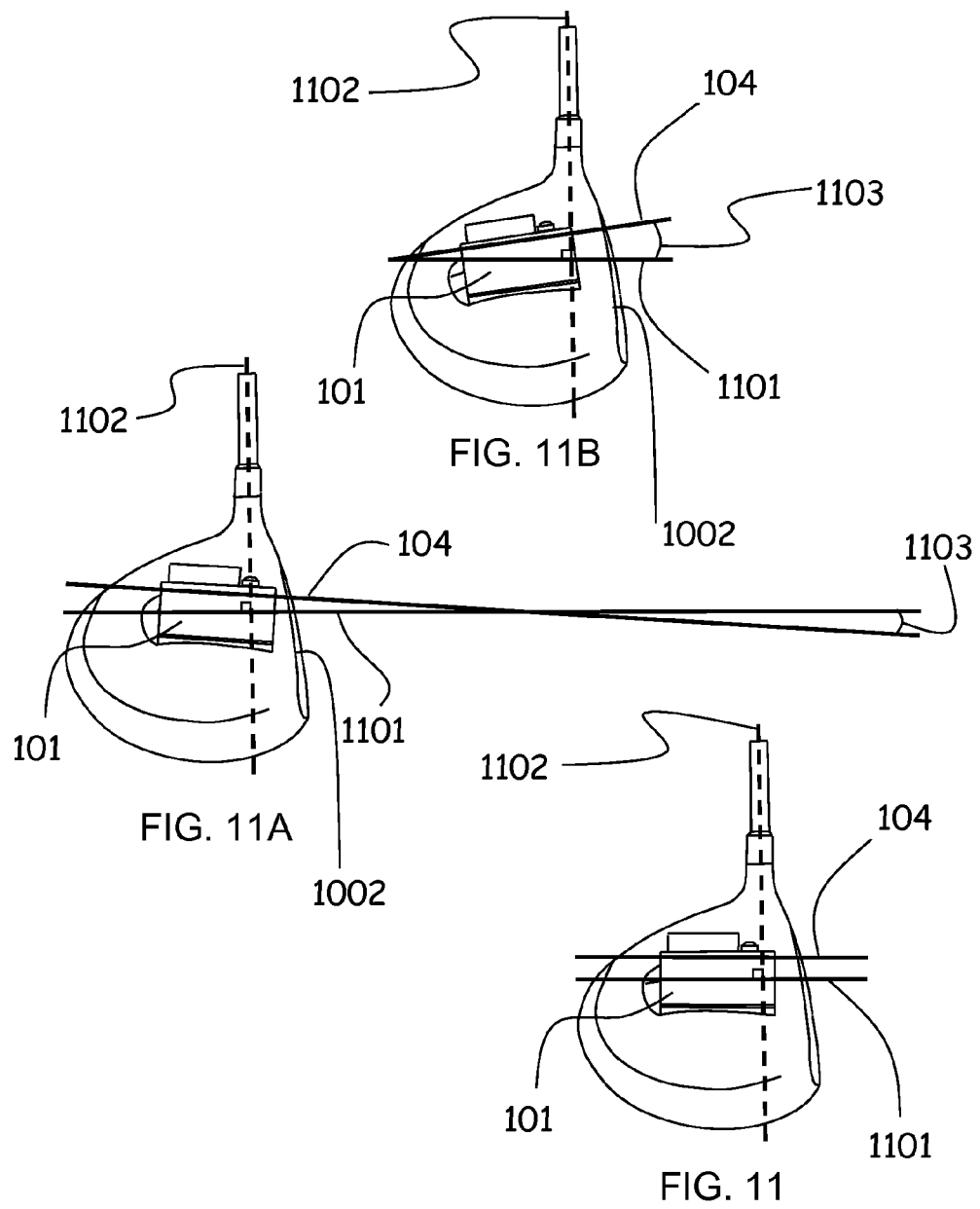
Figure 12:
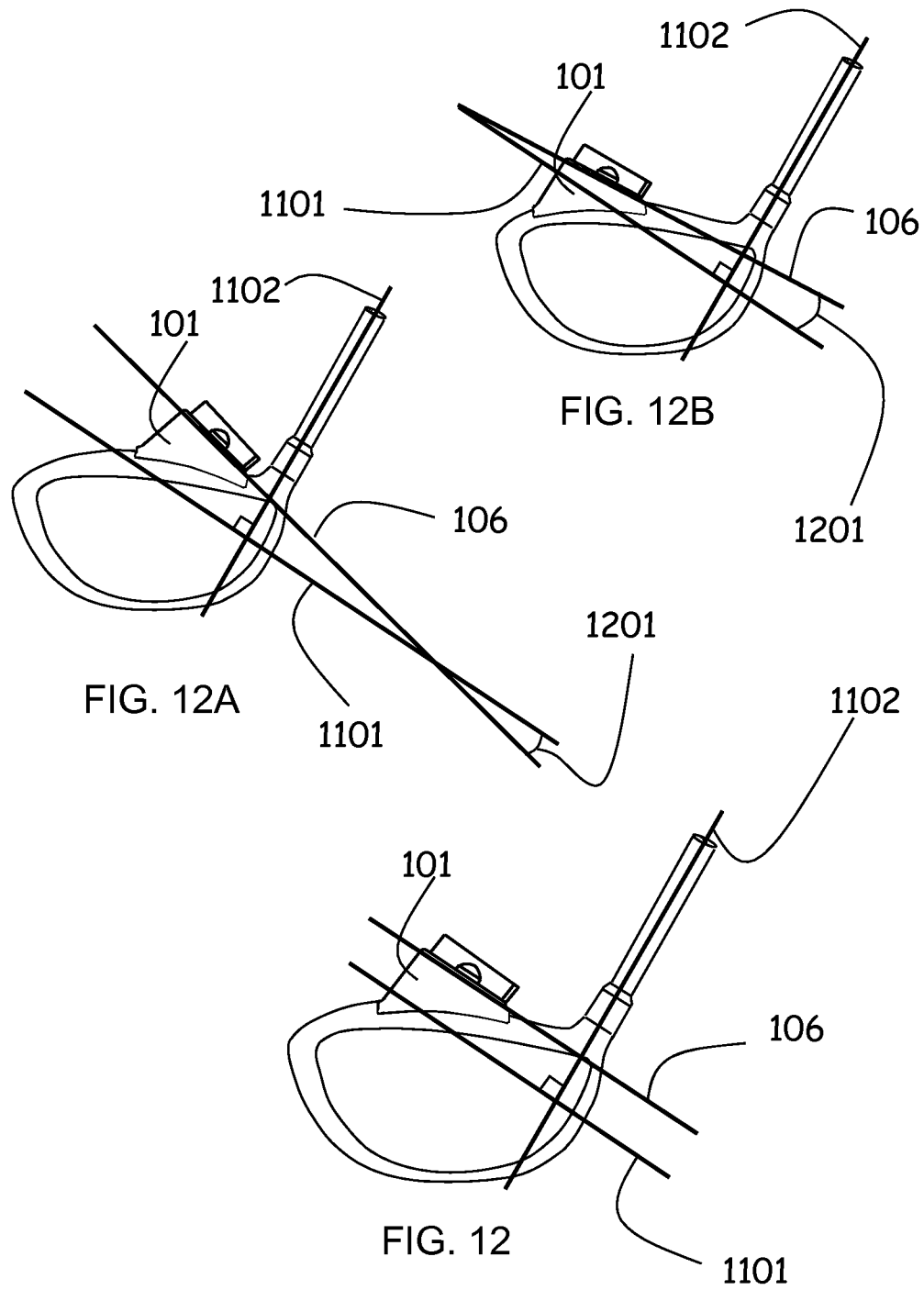

During mounting of the club head module 101, as shown in FIG. 10, the front surface 102 of the club head module 101 can easily be aligned with the club face/club head top surface seam 1002. This alignment results in the $y_f$-axis 106 being parallel to the plane 203 which is the plane created if the club face has zero loft. Using this as the only alignment reference for attaching the club head module 101 to the club head 201, two degrees of freedom still exist that can contribute to club module 101 mounting angle errors. The module 101 mount angle errors can be described with two angles resulting from the following conditions:

1. The module 101 being mounted a greater distance away or closer to the club face seam 1002 causing an angle rotation around the $y_f$-axis 106 causing the $x_f$-axis 104 and $z_f$-axis 105 to be misaligned with their intended club structure references. The mathematical label that describes this angle of rotation is $\lambda$ 1103 (as shown in FIG. 11).
2. The module 101 being mounted closer to or farther away from the club shaft 202 causing an angle rotation around the $x_f$-axis 104 causing the $y_f$-axis 106 and the $z_f$-axis 105 to be misaligned with the intended club structure references. The mathematical label that describes this angle of rotation is $\kappa$ 1201 (as shown in FIG. 12).

The issue of mounting angle variation is most prevalent with the club head module 101 being rotated around the $y_f$-axis. As shown in FIG. 11, the club head module 101 is mounted with the $x_f$-axis 104 parallel to the plane 1101 that is defined as perpendicular to the shaft axis 1102. With this condition met the angle value $\lambda=0$ 1103 indicates no rotation around the $y_f$-axis 106 (not shown but is perpendicular to drawing surface). As shown in FIG. 11A, the club head module 101 is mounted closer to the club face seam 1002 causing a negative value for the angle $\lambda$ 1103 between the plane 1101 and the $x_f$-axis 104. As shown in FIG. 11B, the club head module 101 is mounted further from the seam 1002 resulting in a positive value for the angle $\lambda$ 1103 between the plane 1101 and the $x_f$-axis 104. On a typical club head, and depending on how far back or forward on the club head dome the module 101 is mounted, the mounting error angle $\lambda$ 1103 typically varies between −1 degrees and +6 degrees. This angle creates a small rotation around the $y_f$-axis 106 resulting in a misalignment of the $x_f$-axis 104 and also the $z_f$-axis 105. This mounting error can be experimentally determined using a standard golf swing.

For a linear acceleration path the relationship between true acceleration and that of the misaligned measured value of $a_{sx}$ is given by the following equations where $a_{sx-true}$ is defined as what the measured data would be along the $x_f$-axis 104 with $\lambda=0$ 1103 degrees. A similar definition holds for $a_{sz-true}$ along the $z_f$ axis 105. Then:

$$a_{sx-true}=a_{sx}/\cos(\lambda) \qquad 66.$$

$$a_{sz-true}=a_{sz}/\cos(\lambda) \qquad 67.$$

However, the travel path 307 is not linear for a golf swing which creates a radial component due to the fixed orientation error between the offset module measurement coordinate system and the properly aligned module measurement coordinate system. As a result, any misalignment of the club head module axis by angle $\lambda$ creates an $a_{z-radial}$ component as measured by the misaligned $x_f$-axis 104. The $a_{z\text{-}radial}$ component contributes to the $a_{sx}$ measurement in the following manner:

$$a_{sx} = a_{sx\text{-}true} + a_{sz}\sin(\lambda) \quad 68.$$

The angle $\lambda$ 1103 is constant in relation to the club structure, making the relationship above constant, or always true, for the entire swing. The detection and calibrating correction process of the mounting variation angle $\lambda$ 1103 is determined by examining equations (50) and (53) at the point of maximum velocity where by definition:

η goes to zero $a_{ch}$ goes to zero

Therefore, at maximum velocity $a_{sx\text{-}true}$ must also go to zero. At maximum velocity:

$$69.\ a_{sx\text{-}true} = a_{sx} - a_{sz}\sin(\lambda) = 0$$

$$70.\ \lambda = \sin^{-1}\!\left(\frac{a_{sx}}{a_{sz}}\right)$$

Now the measured data arrays for both the affected measurement axis $x_f$-axis 104 and $z_f$-axis 105 must be updated with calibrated data arrays.

$$a_{sx\text{-}cal} = a_{sx} - a_{sz}\sin\lambda \quad 71.$$

$$a_{sz\text{-}cal} = a_{sz}/\cos\lambda \quad 72.$$

The new calibrated data arrays $a_{sx\text{-}cal}$ and $a_{sz\text{-}cal}$ are now used and replaces all $a_{sx}$ and $a_{sz}$ values in previous equations which completes the detection and calibration of club head module mounting errors due to a error rotation around the $y_f$-axis 106.

Now the final detection and calibration of the club head module 101 mounting error angle κ 1201 around the $x_f$-axis 104 can be done. As shown in FIG. 12, the angle κ 1201 is zero when the club head module 101 is perfectly mounted, defined as when the club head module 101 axis $y_f$-axis 106 is parallel with the plane 1101, that is perpendicular to the shaft axis 1102. As shown in FIG. 12A when the club head module 101 is mounted closer to the shaft the $y_f$-axis 106 intersects the plane 1101 creating a negative value for the angle κ 1201. As shown in FIG. 12B the angle κ 1201 is a positive value resulting from the intersection of the $y_f$-axis 106 and the plane 1101 when the module 101 is mounted further away from the shaft.

The detection of mounting error angle κ 1201 is achieved by evaluating $C_\Omega$ resulting from the iterative solution steps 2 though 4 described earlier. If $C_\Omega$ is not very close or equal to one, then there is an additional $a_z$-radial contribution to $a_{sy}$ from mounting error angle κ 1201. The magnitude of mounting error angle κ 1201 is determined by evaluating $\Omega$ 601 at maximum velocity from equation (64) where for no mounting error $C_\Omega = 1$. Then the mounting angle κ 1201 is determined by:

$$\kappa = (C_\Omega - 1)(dm_s a_{sz}\cos(\eta))/(C(KC + m_s a_{sz}\cos(\eta))) \quad 73.$$

As previously described for mounting angle error $\lambda$, the mounting error angle κ 1201 affects the two measurement sensors along the $y_f$-axis 106 and the $z_f$-axis 105. Consistent with the radial component errors resulting from the $\lambda$ 1201 mounting angle error, the κ 1201 mounting angle error is under the same constraints. Therefore:

$$a_{sy\text{-}cal} = a_{sy} - a_{sz}\sin(\kappa) \quad 74.$$

$$a_{sz\text{-}cal} = a_{sz}/\cos\lambda \quad 75.$$

The new calibrated data arrays $a_{sy\text{-}cal}$ and $a_{sz\text{-}cal}$ are now used and replaces all $a_{sy}$ and $a_{sz}$ values in previous equations which complete the detection and calibration of club head module mounting errors due to a mounting error rotation around the $x_f$-axis 104.

Thereby, the preferred embodiment described above, is able to define the dynamic relationship between the module 101 measured axes coordinate system and the inertial acceleration force axes coordinate system using the multi-lever model and to define all related angle behaviors, including module 101 mounting errors.

All of the dynamically changing golf metrics described as angle and or amplitude values change with respect to time. To visually convey these metrics to the golfer, they are graphed in the form of value versus time. The graphing function can be a separate computer program that retrieves output data from the computational algorithm or the graphing function can be integrated in to a single program that includes the computational algorithm.

The standard golf swing can be broken into four basic interrelated swing segments that include the backswing, pause and reversal, down stroke, also called the power-stroke, and follow-through. With all angles between coordinate systems defined and the ability to separate centrifugal inertial component from inertial spatial translation components for each club head module measured axis, the relationships of the data component dynamics can now be evaluated to define trigger points that can indicate start points, end points, or transition points from one swing segment to another. These trigger points are related to specific samples with specific time relationships defined with all other points, allowing precise time durations for each swing segment to be defined. The logic function that is employed to define a trigger point can vary since there are many different conditional relationships that can be employed to conclude the same trigger point. As an example, the logic to define the trigger point that defines the transition between the back swing segment and the pause and reversal segment is:

If $a_z$-radial(tn)<1.5 g
  AND
  $a_{sx}$-linear(tn)=0
  AND
  AVG($a_{sx}$-linear(tn−5) thru $a_{sx}$-linear(tn))<−1.2 g
  AND
  AVG($a_{sx}$-linear(tn) thru $a_{sx}$-linear(tn+5))>+1.2 g By defining the exact time duration for each swing segment and understanding that each swing segment is related and continuous with an adjacent segment, the golfer can focus improvement strategies more precisely by examining swing segments separately.

By incorporating a low mass object that is used as a substitute strike target for an actual golf ball the time relationship between maximum club head velocity and contact with the strike target can be achieved. The low mass object, such as a golf waffle ball, can create a small perturbation which can be detected by at least one of the sensor measurements without substantially changing the characteristics of the overall measurements. In addition, the mass of the substitute strike object is small enough that it does not substantially change the inertial acceleration forces acting on the club head or the dynamically changing relationship of the inertial axes coordinate system in relation to the module measured axes coordinate system.

The data transfer from the club head module 101 to a user interface can take place in two different ways: 1) wirelessly to a receiver module plugged into a laptop or other smart device, or 2) a wired path to a user module that is attached to the golf club near the golf club grip.

Figure 13:
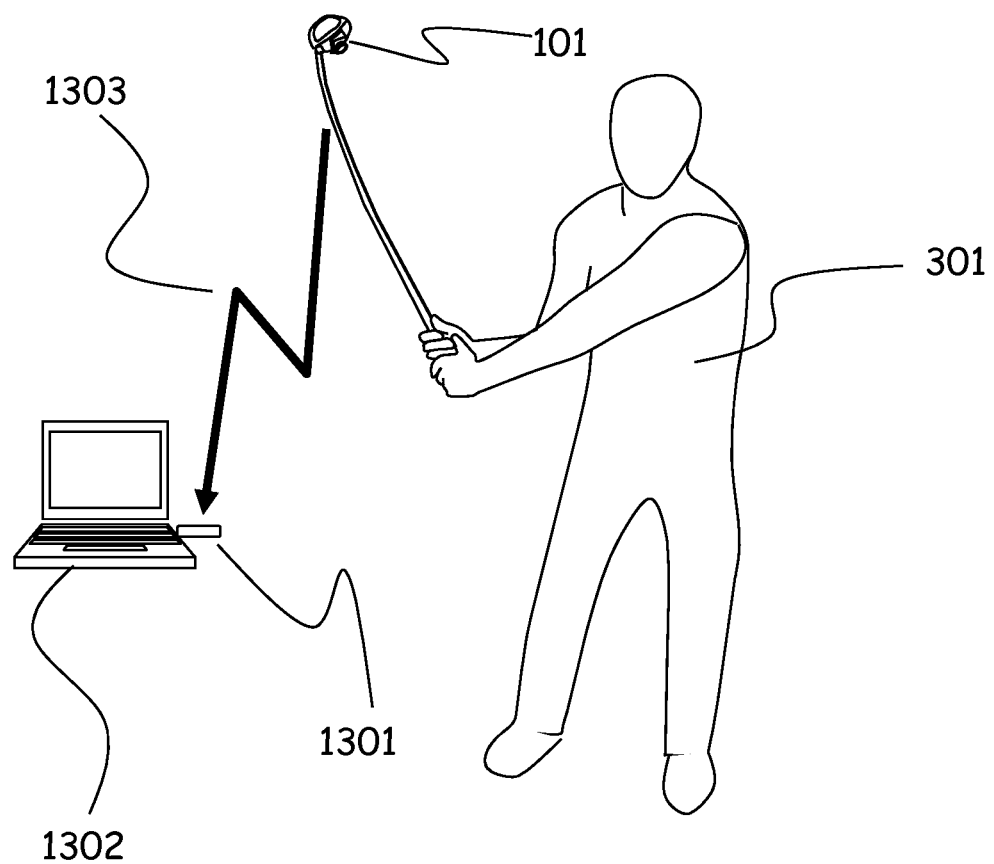
FIG. 13 shows the wireless link between the club head module and the USB receiving unit plugged into a user interface device being a laptop computer.

The preferred embodiment as shown in FIG. 13 demonstrates the module 101 transmitting measured data through a wireless method 1303 to a receiver module 1301 that is plugged into a computer laptop 1302. The receiver module 1301 transfers the data through a USB port to the computer laptop 1302 where the data is processed by the computational algorithm and displayed to the golfer 301.

Figure 14:
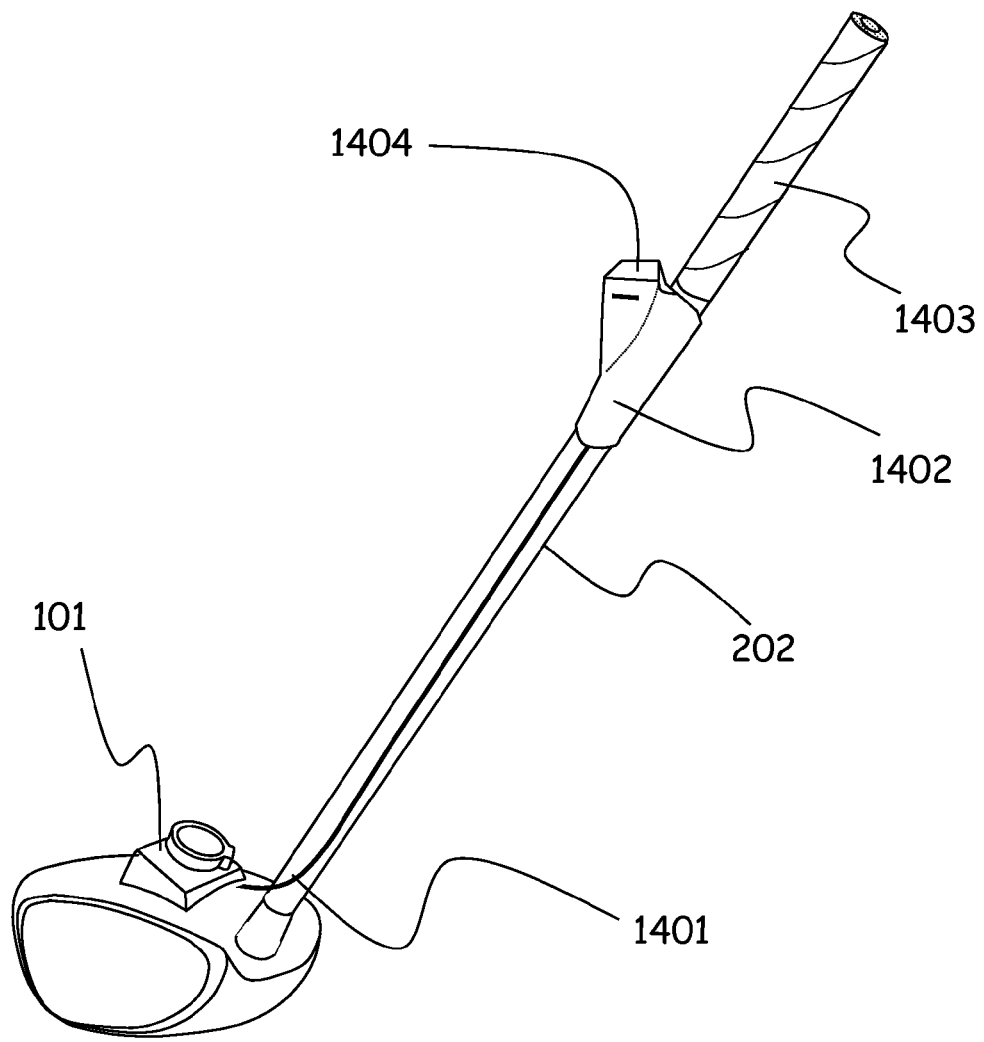
FIG. 14 shows a wired connection between the club head module and a custom user interface unit attached to the club shaft.

In another embodiment, as shown in FIG. 14, the club head module 101 communicates swing data through a wired connection 1401 to a user interface module 1402 that is attached to the club shaft 202 below the grip 1403. The interface module 1402 contains the processing power to compute the metrics and display those metrics on the graphical and text display 1404.

The approach developed above can also be applied for a golf club swing when the golf club head contacts the golf ball. For this case, the above analysis returns the values of the three angles and club head velocity just before impact. Using these values along with the sensor measurements after impact describing the change in momentum and the abrupt orientation change between the module's measured sensor coordinate system and the inertial motional acceleration force coordinate system will enable the determination of where on the club head face the ball was hit, and the golf ball velocity.

The ability to correlate the acceleration measurements and resulting dynamics golf metrics time line to a spatial reference allows key dynamics swing metrics to be further evaluated in the contexts of space. This offers golfers great analytical benefit when evaluating a free golf swing that does not impact an object. The swing metrics can be analyzed in relation to key spatial reference locations, such as anticipated ball location, peak elevation of backswing, peak elevation of power-stroke, peak elevation of follow through and others such as club head travel path 90 degrees out from right or left shoulder. These spatial reference points all offer their own set of benefits when analyzing the varied dynamic swing metrics in reference to spatial locations near the club head travel path. True swing efficiency and effectiveness can now be evaluate without the motional perturbations that occur when the golf club strikes and object such as a golf ball. The benefit of analyzing a free swing as opposed to an impact swing can be demonstrated with a fundamental example of evaluating swing efficiency with respect to the dynamic swing metric of club head velocity which is directly related to achievable ball trajectory distance. In this example a golfer may want to improve and optimize their swing style for maximum distance. Using free swing measurements and analysis that provides dynamic club head velocity in relation to an anticipated ball location allows the golfer to evaluate if they are reaching maximum club head velocity before, at, or after the anticipated ball location. This is not possible with club/ball impact because of the abrupt velocity reduction resulting from impact eliminating the ability to determine where maximum velocity would have occurred after impact. Further, the swing style can be modified for maximum power and efficiency by aligning club head maximum velocity with anticipated ball location for maximum energy transfer at anticipated ball location. The same benefit themes demonstrated with the club head velocity example also can be applied to all dynamics swing metrics such as but not limited to, club head spatial acceleration and maximum club head spatial acceleration, club face angle and where the club face angle reached a square position, shaft flex lag/lead angle and many others.

These measurement and evaluation capabilities are not available with conventional swing analyzers that rely impacting with a golf ball, because the impact itself abruptly changes all swing metrics including club head orientation, club head motion and shaft actions and therefore eliminates the possibility of comprehensive analysis of true swing performance.

Several embodiments of correlation methods are demonstrated using the integration of conventional Receiver Signal Strength Indicator (also referred to as RSSI) functionality into the previously recited swing measurement and analysis system. The system uses RSSI to determine relative spatial relationships between the Club Head Module 101 (first module) and the USB Module 1301 (second module) during the entire swing. The spatial relationships, such as nearest together or farthest apart or equivalents or ratios are used to identify club head location(s) at a point or points in time that correspond to time location(s) on the acceleration measurement time line thereby correlating space an time.

Figure 15:
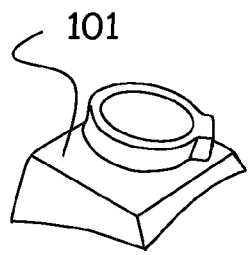
FIGS. 15, 15A, 15B, and 15C show the system components and their electronic functions respectively for the first embodiment of time space correlation defining a relationship between the measurements time line and the spatial domain.
Figure 15A:
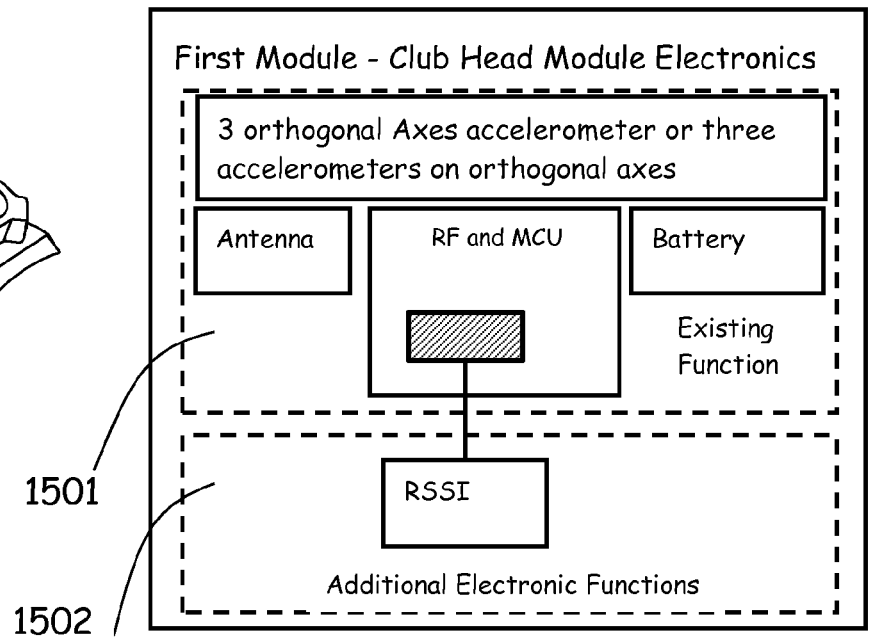

As shown in FIGS. 15 and 15A of the first embodiment of the time-space correlation, the Club Head Module 101 (first module) comprises all existing electronics functions 1501, that include: a means of measurement of three orthogonal acceleration axes, implemented with a three axis accelerometer device or a combination of single or dual axis accelerometer devices to achieve acceleration measurement of three orthogonal axes, a means for an antenna that can be a PC embedded antenna or a chip component antenna, RF wireless communication functions providing a means for transmitting RF signals and a means of receiving RF signals implemented with common off the shelf RF integrated circuit device(s), circuit control and data processing and data formatting functions that provide a means for controlling all circuit functions, a means for data acquisition and a means for formatting data for various protocol structures all implemented with a common off the shelf integrated circuit device typically labeled MCU or Micro Controller Unit, an energy source function providing a means for an energy supply to operate circuitry and is implemented with a battery device. Further the Club Head Module 101 (first module) comprises additional electronic functionality 1502 that includes a means for measuring receiver signal strength that is implemented with common off the shelf RSSI circuitry that may be included in common off the shelf RF integrated circuits devices.

Figure 15B:
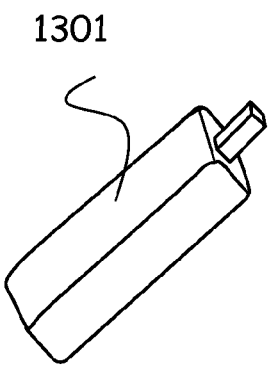
Figure 15C:
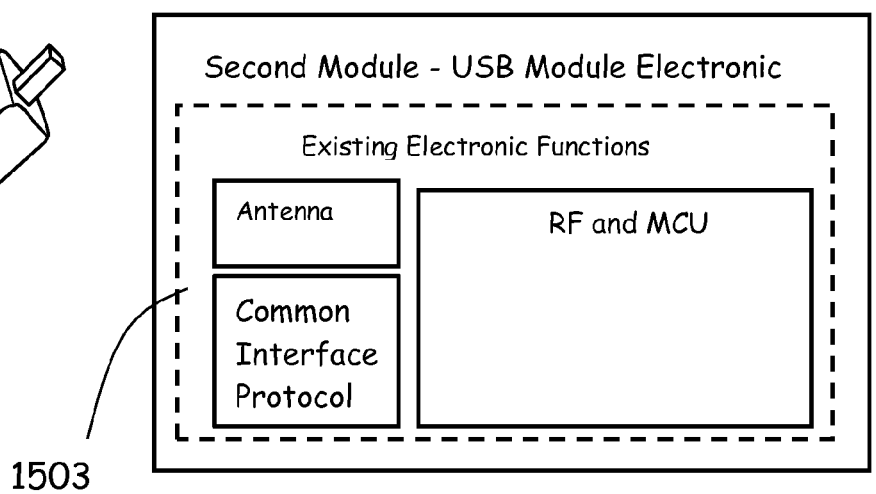

As shown in FIGS. 15B and 15C of the first embodiment of the time-space correlation, the USB Module 1301 (second module) comprises all earlier recited existing electronic functions 1503 including an antenna function providing a means for an omni-directional or near omni-direction RF antenna that can be implemented as a PCB (Parts Circuit Board) embedded antenna or a chip component surface mount antenna device, RF wireless communication functions providing a means for transmitting RF signals and a means of receiving RF signals implemented with common off the shelf RF integrated circuit device(s), a means for data acquisition and a means for formatting data and a means for bidirectional communication using standard common interface protocols for transmitting data to and receiving data from a user interface device all implemented with a common off the shelf integrated circuit device typically labeled MCU or Micro Controller Unit, and in this example the common interface protocol is consistent with a USB port.

Figures 16A, 16B:
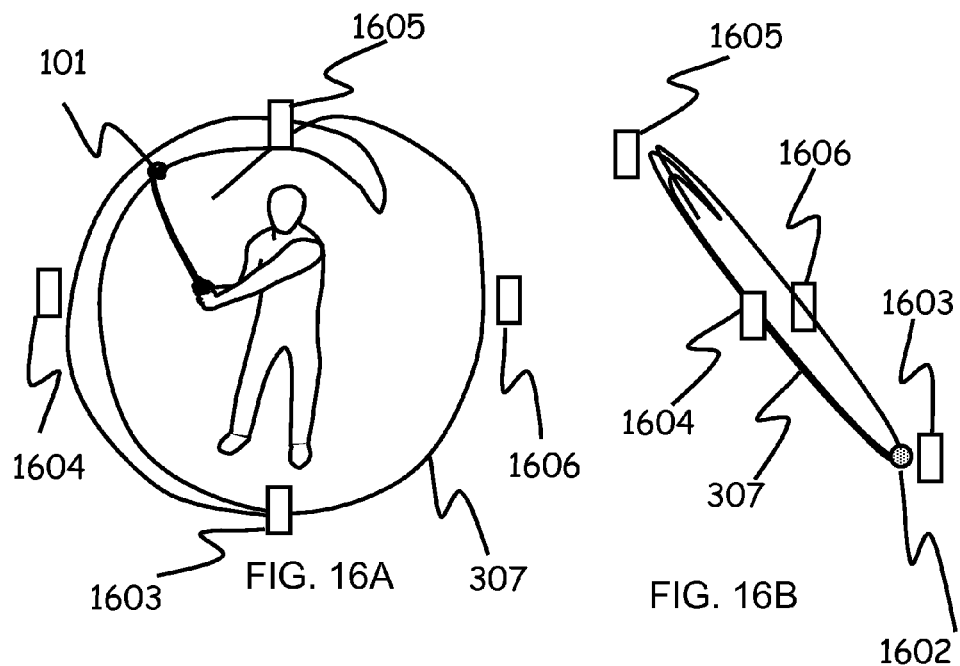
FIGS. 16, 16A and 16B show the system setup, configuration example options and operation of the first, second and forth embodiments of the time space correlation.
Figure 16:
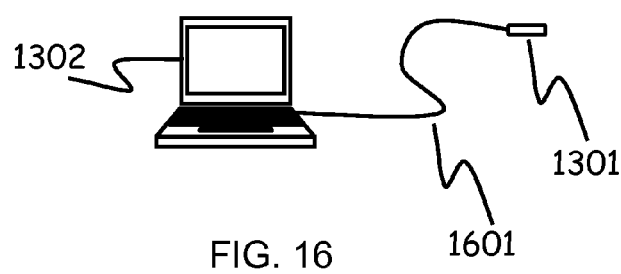

FIGS. 16, 16A and 16B of the first embodiment of the time-space correlation shows the system configuration and operation. As shown in FIG. 16 the system comprising a user interface 1302 (a laptop in this example) with computation engine, display and standard input output port connections, in this example a USB port and is connect to a USB Cable 1601 (wired connection) that is further connected to USB Module 1301 (second module). The USB module 1301 (second module) is placed remotely from user interface 1302 at a predetermine location. FIGS. 16A and 16B show a front view perspective and a side view perspective respectively of the club head travel path 307 of a golf swing and FIG. 16B further shows an anticipated location of a golf ball 1602. A predetermined single location can be anywhere near the anticipated golf head travel path 307. Examples of predetermined location options can include, but not limited to, location 1603, 1604, 1605 and 1606. In this embodiment the USB module 1301 is located at predetermined location 1603 that is close to club head travel path 307 and in front of anticipated ball location 1602. Operationally, the golfer takes a swing, the Club Head Module 101 (first module) attached to club head top surface, travels along the club head travel path 307 and simultaneously Club Head Module 101 measures three dimensional acceleration and synchronously and time aligned measures received strength for received wireless signal transmitted by USB module 1301. Further, Club Head Module 101 (first module) is capturing and transmitting measurement data comprising acceleration and received signal strength measurements to USB Module 1301 for further transport to User Interface 1302 with computational engine.

A software application of the first embodiment of the time-space correlation resides on User Interface 1302 computational engine and comprising all functions for user interface, display and data processing of measurements within software application. The data processing of measurements includes the previously recited algorithms for club head alignment calibration and acceleration data analysis. Further, software application implements a third algorithm that processes the receiver signal strength measurements in conjunction with synchronized acceleration measurements to determine time space correlation. The third algorithm processes steps of the first embodiment of the time-space correlation include the step of:
1. Digitally low pass filter RSSI measured time line data to reduce effects of RF multipath fading
2. Processes filtered RSSI data using peak detection and minimum detection methods to determine time points on time line of highest and lowest signal strength
3. Flag and label time point of peak RSSI measurement defining the relationship of Club Head Module 101 and USB Module 1301 at minimum spatial separation.
4. Flag and label time point of minimum RSSI measurement defining the spatial relationship of Club Head Module 101 and USB Module 1301 at maximum spatial separation.
5. Label the correlated time points on the acceleration measurements and dynamics golf metrics results time line defining space time relationship.

Figure 17:
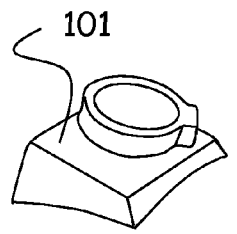
FIGS. 17, 17A, 17B and 17C show the system components and their electronic functions respectively for the second embodiment of time space correlation defining a relationship between the measurements time line and the spatial domain.
Figure 17A:
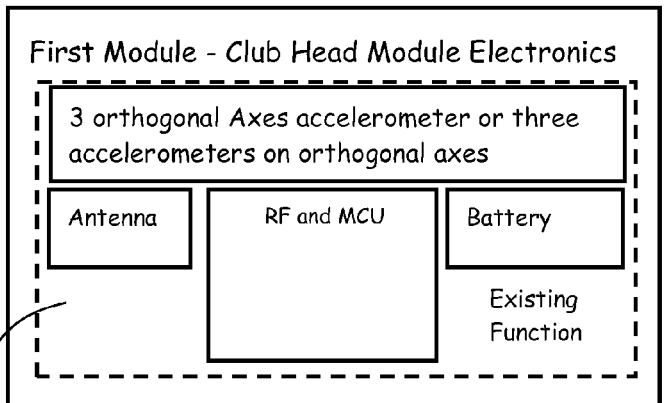

As shown in FIGS. 17 and 17A of the second embodiment of the time-space correlation, the Club Head Module 101 (first module), comprises all existing electronics functions 1701, that include a means of measurement of three orthogonal acceleration axes, that can include but are not limited to the use of a three axis accelerometer device or a combination of single or dual axis accelerometer devices to achieve acceleration measurement of three orthogonal axes, a means for an antenna that can be a PCB embedded antenna or a chip component antenna, RF wireless communication functions providing a means for transmitting RF signals and a means of receiving RF signals implemented with common off the shelf RF integrated circuit device(s), circuit control and data processing and data formatting functions that provide a means for controlling all circuit functions, a means for data acquisition and a means for formatting data for various protocol structure all implemented with a common off the shelf integrated circuit device typically labeled MCU or Micro Controller Unit, an energy source function providing a means for an energy supply to operate circuitry and implemented with a battery device.

Figure 17B:
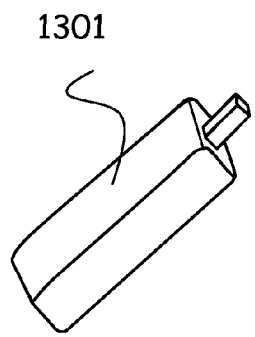
Figure 17C:
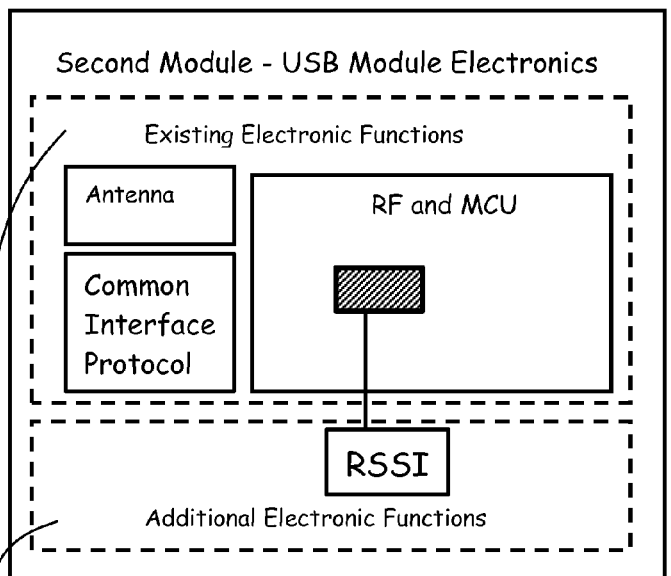

As shown in FIGS. 17B and 17C of the second embodiment of the time-space correlation, the USB Module 1301 (second module) comprises all earlier recited existing electronic functions 1702 including an antenna function providing a means for an omni-directional or near omni-direction or semi-omni directional RF antenna that can be implemented as a PCB (Parts Circuit Board) embedded antenna or a chip component surface mount antenna device or a stand-alone antenna device, RF wireless communication functions providing a means for transmitting RF signals and a means of receiving RF signals implemented with common off the shelf RF integrated circuit device(s), control, capture and formatting functions that provide a means for controlling all circuit operations, a means for data acquisition and a means for formatting data and a means for bidirectional communication using standard common interface protocols for transmitting and receiving data from a user interface device all implemented with a common off the shelf integrated circuit device typically labeled MCU or Micro Controller Unit, and in this embodiment the common interface protocol is consistent with a USB port. Further the USB Module 1301 (second module) comprises additional electronic functionality 1703 that includes a means for measuring receiver signal strength that is implemented with common off the shelf RSSI circuitry that typically can be included in common off the shelf RF integrated circuits devices.

FIGS. 16, 16A and 16B of the second embodiment of the time-space correlation shows the system configuration and operation. As shown in FIG. 16 the system comprising a user interface 1302 (a laptop in this example) with computation engine, display and standard input output port connections, in this example a USB port and is connect to a USB cable 1601 (wired connection) that is further connected to USB Module 1301 (second module). The USB module 1301 (second module) is placed remotely from user interface 1302 at a predetermine location. FIGS. 16A and 16B shows a front view perspective and a side view perspective respectively of the club head travel path 307 of a golf swing and FIG. 16B further shows an anticipated location of a golf ball 1602. The predetermined single location can be anywhere near the anticipated golf club head travel path 307. Examples of predetermined location options can include but are not limited to locations 1603, 1604, 1605 and 1606. In this example the USB module 1301 (second module) is located at predetermined location 1603 that is close to club head travel path 307 and in front of anticipated ball location 1602. Operationally, the golfer takes a swing, the Club Head Module 101 (first module) travels along the club head travel path 307 and Club Head Module 101 (first module) transmits wireless signal carrying acceleration measurement to USB Module 1301 (second module). USB Module 1301 (second module) receives wireless signal carrying acceleration measurements and measures received signal strength of signal carrying acceleration measurements. USB Module 1301 (second module) further combines acceleration and received signal strength measurements together in a synchronized fashion and further transmits combined measurements through USB cable to User Interface 1302 computation engine.

A software application of the second embodiment of the time-space correlation, resides on User Interface 1302 computational engine and comprising all functions for User Interface's 1302, display and data processing of measurements within software application. The data processing of measurements includes the previously recited algorithms for Club Head Module 101 Alignment Calibration and Acceleration Data Analysis. Further, software application implements a third algorithm that processes the receiver signal strength measurements in conjunction with synchronized acceleration measurements to determine time space correlation. The third algorithm of the second embodiment of the time-space correlation includes the steps of:

1. A means of calculating time delay between measurements made at Club Head Module 101 (first module) and measurements made at USB Module 1301 (second module) comprising the steps of:
   a. Define time duration of processing at Club Head Module 101 after acceleration signal is in a sample and hold state by multiplying the time duration of 1 instruction multiplied by number of instruction to complete the following tasks
      i. Data capture
      ii. Data formatting for wireless transmission protocol
   b. If wireless communication protocol uses Time Division Multiple Access (TDMA) structure, define the time duration between wireless packet transmissions based on that predefined structure.
   c. Define time duration of signal propagation=0
   d. Define time duration of processing at USB Module 1301 by multiplying the time duration of 1 instruction multiplied by number of instruction to complete the following tasks:
      i. receive and demodulate Club Head Module 101 transmitted signal
      ii. Receiver signal strength output from RSSI circuitry at a sample and hold state for measurement
   e. Sum steps (a.) and (b.) and (c.) and (d.) together to define time delay between measurements to define time delay between Club Head Module 101 measurements and USB Module 1302 measurements
2. Time shift the measurement time line taken at the Club Head Module 101 (first module) in relation to measurements time line taken at USB Module 1301 (second module) by said time delay to define a single time line comprising all measurements synchronized and aligned in time.
3. Digitally low pass filter RSSI measured time line data to reduce effects of RF multipath fading
4. Processes filtered RSSI data using peak detection and minimum detection methods to determine time points on time line of highest and lowest signal strength
5. Flag and label time point of peak RSSI measurement defining the relationship of Club Head Module 101 and USB Module 1301 at minimum spatial separation.
6. Flag and label time point of minimum RSSI measurement defining the spatial relationship of Club Head Module 101 and USB Module 1301 at maximum spatial separation.
7. Label the correlated time points with acceleration measurements and resulting dynamics golf metrics time line defining space time relationship.

As shown in FIGS. 17 and 17A of the third embodiment of the time-space correlation, the Club Head Module 101 (first module), comprises all existing electronics functions 1701, that include a means of measurement of three orthogonal acceleration axes, that can be implemented with but are not limited to the use of a three axis accelerometer device or any combination of single or dual axes accelerometer devices to achieve acceleration measurement of three orthogonal axes, a means for an antenna that can be implemented with a PCB embedded antenna or a chip component antenna, RF wireless communication functions providing a means for transmitting RF signals and a means of receiving RF signals implemented with common off the shelf RF integrated circuit device(s), circuit control and data processing and data formatting functions that provide a means for controlling all circuit functions, a means for data acquisition and a means for formatting data for various protocol structure all implemented with a common off the shelf integrated circuit device(s) typically labeled MCU or Micro Controller Unit, an energy source function providing a means for an energy supply to operate circuitry and implemented with a battery device.

Figure 18:
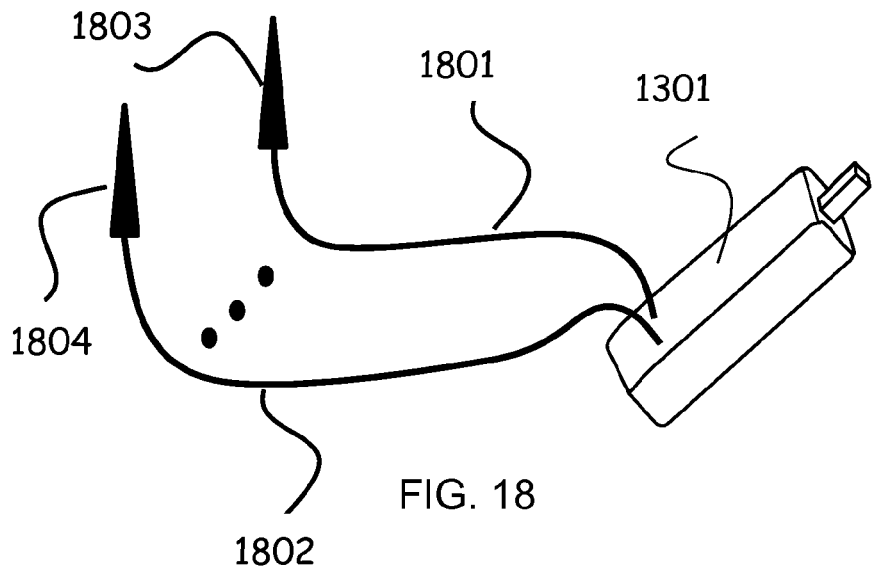
FIGS. 18 and 18A show the USB Module 1302 and external antennas and the electronic functions within the USB Module for the third embodiment of the time space correlation defining a relationship between the measurements time line and the spatial domain.
Figure 18A:
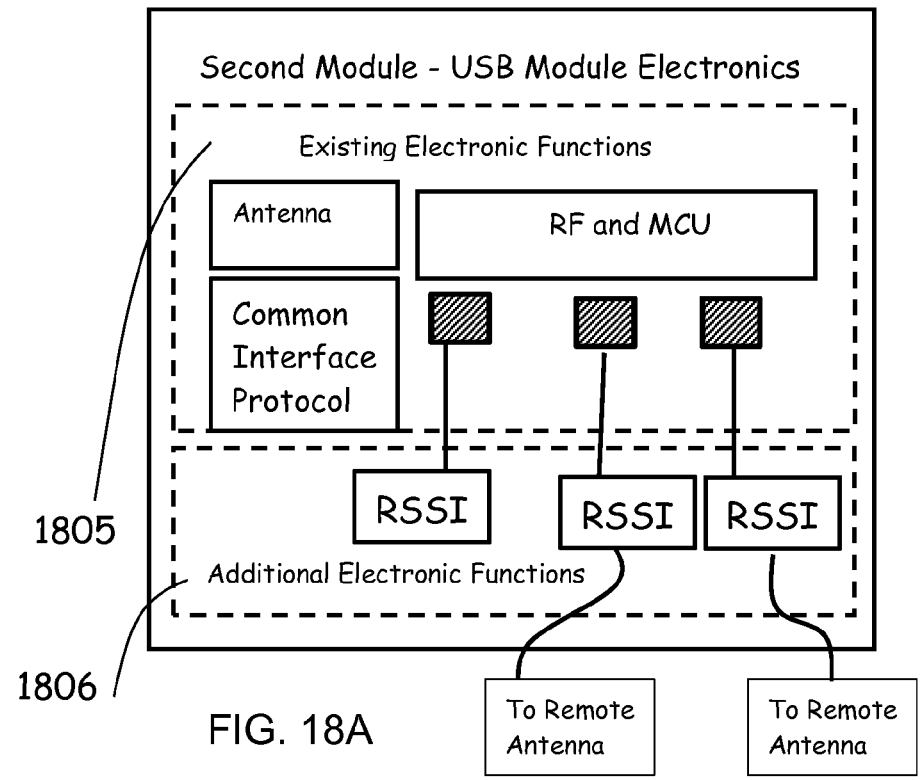

As shown in FIGS. 18 and 18A of the third embodiment of the time-space correlation the USB Module 1301 (second module) has addition connections comprising electrical connectivity to one or more wired coaxial cables 1801 and or 1802 that further electrically connect to one or more omni-directional or near omni-direction external antennas 1803 and or 1804. As shown in FIG. 18A, USB Module 1301 (second module) comprises earlier recited existing electronic functions 1805 including an antenna function providing a means for an omni-directional or near omni-directional RF antenna that can be implemented as a PCB (Parts Circuit Board) embedded antenna or a chip component surface mount antenna device or other, RF wireless communication functions providing a means for transmitting RF signals and a means of receiving RF signals implemented with common off the shelf RF integrated circuit device(s), a means for data acquisition and a means for formatting data and a means for bidirectional communication using standard common interface protocols for transmitting and receiving data to and from a user interface device all means implemented with a common off the shelf integrated circuit device typically labeled MCU or Micro Controller Unit, and in this example the common interface protocol is consistent with a USB port. Further, USB Module 1301 (second module) comprises additional electronic functionality 1806 that includes a means for measuring receiver signal strength of one antenna within USB Module 1301 (second module) and a means for measuring receiver signal strength of one or more external remote antennas. In this embodiment a means for measuring signal strength at remote antennas 1803 and 1804. The receiver signal strength measurement functions provide a means for measuring signal strength of all antennas separately and can be implemented with separate RSSI circuitries that can be integrated into a single RF integrated circuit device or implemented with separate RSSI circuitry each being a separate integrated circuit device.

FIGS. 19, 19A and 19B of the third embodiment of the time-space correlation shows the system configuration and operation. As shown in FIG. 19 the system comprising a User Interface 1302 (a laptop in this example) with computation engine, display and standard input output port connections, and in this example the port connection is a USB port and is connect to a USB Cable 1601 (wired connection) that is further connected to USB Module 1301 (second module). The USB Module 1301 (second module) is placed remotely from user interface 1302 at a predetermine location. FIGS. 16A and 16B show a front view perspective and a side view perspective respectively of the club head travel path 307 of a golf swing and further FIG. 16B shows an anticipated location of a golf ball 1602. The placement of USB Module 1301 (second module) and remote antennas 1803 and 1804 can be any combination of separate predetermined location near the anticipated golf head travel path 307. Further the spatial club head location during any point in the swing can be defined in in terms of one dimension, two dimensions or three dimensions. The presented example system configuration and operation that is not intended to limit the scope of invention in any way is presented. As shown in FIGS. 19a and 19B for this example, the placement for the USB Module 1301(second module) is at predetermined location 1603 that is near the anticipated club head travel path 307 and in front of the anticipated ball location 1602. Further in this example, first remote antenna 1803 is place at predetermine location 1901 that is near and below club head travel path, and second remote antenna 1804 is placed at predetermined location 1902 that is near and above anticipated club head travel path 307 and may be vertically aligned with predetermined location 1901.

The system operation as shown in FIGS. 19A and 19B for this example includes, the golfer takes a swing, the Club Head Module 101 (first module) travels along a club head travel path 307 and Club Head Module 101 transmits out wireless signal carrying acceleration measurements. Further USB Module 1301 (second module) and remote antennas 1803 and 1804 receive wireless signal carrying acceleration measurements and further USB Module 1301 (second module) separately measures synchronously received signal strength of all antennas. USB Module 1301 (second module) further combines acceleration measurements and all received signal strength measurements together in a synchronized fashion and further transmits combined measurements through USB cable to User Interface 1302 computation engine.

A software application of the third embodiment of the time-space correlation for this example, resides on User Interface 1302 computational engine and comprising all functions for User Interface, display and data processing of measurements within software application. The data processing of measurements includes the previously recited algorithms for Club Head Module 101 alignment calibration and acceleration data analysis. Further, software application implements a third algorithm that processes all receiver signal strength measurements from all antennas in conjunction with synchronized acceleration measurements to determine time space correlation. The third algorithm of the third embodiment of the time-space correlation include the steps of:

1. A means of calculating time delay between measurements made at Club Head Module 101 (first module) and synchronized measurements made at USB Module 1301 (second module) for internal and remote antennas comprising the steps of:
   a. Define time duration of processing at Club Head Module 101 after acceleration signal is in a sample and hold state by multiplying the time duration of 1 instruction multiplied by number of instruction to complete the following tasks
      i. Data capture
      ii. Data formatting for wireless transmission protocol
   b. If wireless communication protocol uses Time Division Multiple Access (TDMA) structure, define the time duration between wireless packet transmissions based on that predefined structure.
   c. Define time duration of signal propagation=0
   d. Define time duration of processing at USB Module 1301 by multiplying the time duration of 1 instruction multiplied by number of instruction to complete the following tasks:
      i. receive and demodulate Club Head Module 101 transmitted signal
      ii. Receiver signal strength output from parallel RSSI circuitries at a sample and hold state for measurement
   e. Sum steps (a.) and (b.) and (c.) and (d.) together to define time delay between measurements to define time delay between Club Head Module 101 measurements and USB Module 1302 measurements
2. Time shift the measurement time line taken at the Club Head Module 101 (first module) in relation to the synchronized group of received signal strength measurements time line taken at USB Module 1301 (second module) for internal and remote antennas 1803 and 1804 to define a single time line with calculated said time delay between measurements removed.
3. Digitally low pass filter all RSSI measurements time lines separately to reduce effects of RF multipath fading.
4. Processes each filtered RSSI data set separately using peak detection and minimum detection methods to determine time points on time line of highest and lowest signal strength for each predetermined location
5. Process each filtered RSSI data set in relation to one another and evaluate for equivalent RSSI measurements at a single time point.
6. Flag and label each time point of each peak RSSI measurement time line defining the relationship of Club Head Module 101 and USB Module 1301 at minimum spatial separation and further Club Head Module 101 and each remote antenna at minimum spatial separations.
7. Flag and label each time point of each minimum RSSI measurement time line defining the relationship of Club Head Module 101 and USB Module 1301 at maximum spatial separation and further Club Head Module 101 and each remote antenna at maximum spatial separations.
8. Flag and label each time point of each occurrence when two RSSI measurements time lines are equivalent at the same time point defining the relationship of Club Head Module 101 and any two antennas have equal spatial separation.
9. Label the correlated time points with acceleration measurements and resulting dynamics golf metrics time line defining time space relationship.
10. Use flagged time line points and predetermined locations of each antenna to map 3 dimension space club head travel on club head travel path.

Invention anticipates that using three antenna located at any three predefined locations can map spatial club head travel in three dimension and correlate to acceleration measurement time line, however, portions of club head travel path can be more accurately represent spatially while reducing accuracy of other portions of the swing, with strategic predetermined locations focusing on providing more accuracy to a given portion or portions of a swing. In the example recited above the accuracy of the backswing and the power-stroke along with anticipated ball location have emphasis with regards to accuracy. In addition use of more than three antennas each with a predetermined location can increase three dimensional spatial accuracy of club head travel path over broader coverage of entire swing.

A forth embodiment of the time space correlation system provides for RSSI measurement capabilities at both the Club Head Module 101 (first module) as described in first embodiment and shown in FIGS. 15, 15A and at the USB Module 1301 (second module) as described in the second embodiment and shown in FIGS. 17B, 17C. The redundant nature of RSSI measurement made at Club Head Module 101(first module) and USB Module 1301 (second module) offer benefits in two areas. The first benefit is that the delay between measurements made at the Club Head Module 101 (first module) and measurements made at the USB Module 1301 (second Module) can be compared directly to define the time delay between measurement modules by analyzing the time separation of peak RSSI measurement made at each of the modules. This is in contrast to the earlier recited second and third embodiments of time space correlation that calculate time delay based on the Club Head Module 101 (first module) and USB Module 1301 (second module) electronic processing time of the electronic functions that include data capture, data formatting for transmission over RF wireless channel and received data formatting at the USB Module 1301 (second module). The second benefit is the reduced effects of multipath fading because the overall RSSI vs. time curves for both RSSI measurements should be identical with the exception of multipath fading characteristics. These benefits effectively simplify the algorithm for calculating the time space correlation.

FIGS. 16, 16A and 16B, of the fourth embodiment of the time-space correlation show the system configuration and operation. As shown in FIG. 16 the system comprising a user interface 1302 (a laptop in this example) with computation engine, display and standard input output port connections, in this example a USB port and is connect to a USB Cable 1601 (wired connection) that is further connected to USB Module 1301 (second module). The USB module 1301 (second module) is placed remotely from user interface 1302 at a predetermine location. FIGS. 16A and 16B shows a front view perspective and a side view perspective respectively of the club head travel path 307 of a golf swing and FIG. 16B further shows an anticipated location of a golf ball 1602. The predetermined location can be anywhere near the anticipated golf head travel path 307. Examples of predetermined location options can include but not limited to location 1603, 1604, 1605 and 1606. In this example the USB module 1301 is located at predetermined location 1603 that is close to club head travel path 307 and in front of anticipated golf ball location 1602. Operationally, the golfer takes a swing, the Club Head Module 101 (first module) travels along the club head travel path 307 and Club Head Module 101 (first module) measures acceleration and measures receiver signal strength of a signal transmitted from USB Module 1301 (second). Further Club Head Module 101 (first module) transmits measured acceleration and receiver signal strength measurements with a wireless signal to USB Module 1301. Further USB Module 1301 receives wireless signal carrying Club Head Module 101 measurements and USB Module 1301 measures received signal strength of signal carrying Club Head Module transmitted measurements. Further, USB Module combines measurements made at Club Head Module 101 and USB Module 1301 in a synchronized fashion and transports all measurements to a user interface with a computation engine.

A software application of the fourth embodiment of the time-space correlation for this example, resides on User Interface 1302 computational engine and comprising all functions for User Interface, display and data processing of measurements within software application. The data processing of measurements includes the previously recited algorithms for Club Head Module 101 alignment calibration and acceleration data analysis. Further, software application implements a third algorithm that processes all receiver signal strength measurements from all antennas in conjunction with synchronized acceleration measurements to determine time space correlation. The third algorithm of the fourth embodiment of the time-space correlation includes the steps of:

1. Digitally low pass filter Club Head Module 101 (first module) RSSI measured time line data to reduce effects of RF multipath fading
2. Digitally low pass filter USB Module (second module) RSSI measured time line data to reduce effects of RF multipath fading
3. Processes both filtered RSSI time line measurements separately using peak detection and minimum detection methods to determine time points on time line of highest and lowest signal strength
4. Define time delay as time separation between RSSI measurements peaks taken at Club Head Module 101 (first module) and USB Module 1301 (second module)
5. Time shift Club Head Module 101 (first module) measurement time line in relation to USB Module (101) measurement time line by said time delay to define a single time line comprising all measurements synchronized and aligned in time with respect to time of measurement.
6. Flag and label time point of peak RSSI measurement defining the relationship of Club Head Module 101 and USB Module 1301 at minimum spatial separation.
7. Flag and label time point of minimum RSSI measurement defining the spatial relationship of Club Head Module 101 and USB Module 1301 at maximum spatial separation.
8. Label the correlated time points with acceleration measurements and resulting dynamics golf metrics time line defining time space correlation.

It is also anticipated that other embodiment arrangements of RSSI measurements exist and are covered by this invention. The may include a combination of embodiments 3 and 4 where RSSI is measure at Club Head Module 101 and USB Module 1301 connected further with remote antennas that transit signal and measure RSSI of received signals.

Figure 20:
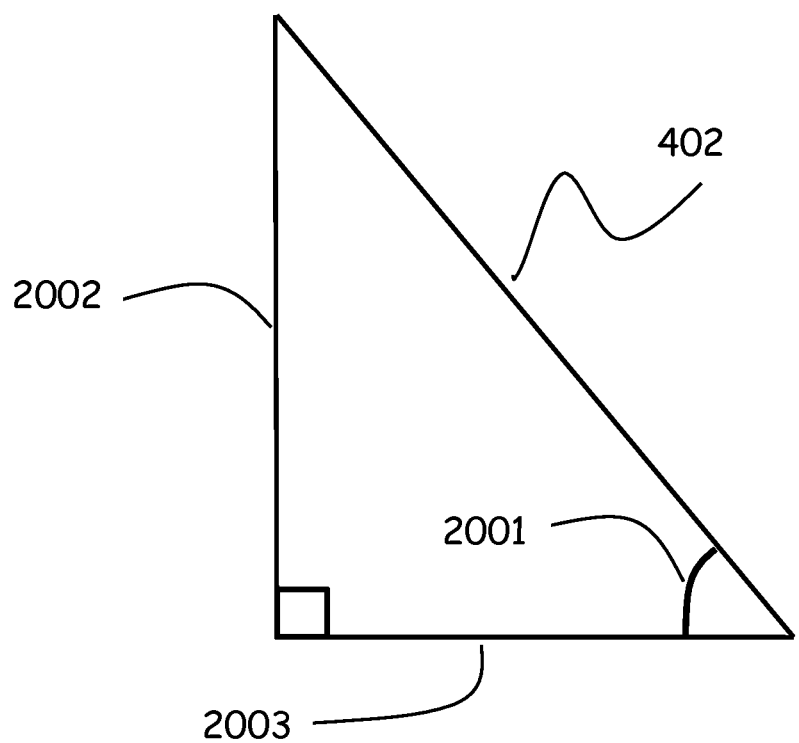
FIG. 20 shows the triangle for calculating swing plain angle to the ground.

As shown in FIG. 20, the time space correlations of embodiments one or two or four enables for the estimation of swing plane angle 2001 in relation to ground plain. The means of calculating a line 402 and it's angle 2001 to the ground that is coincident with swing plane is accomplished with the addition user input into the system that includes the shoulder height 2002 of the golfer. A right triangle is defined with shoulder height 2002 of golfer being one side of triangle that is perpendicular with triangle side 2003 that is coincident with ground plain and dynamic swing radius 402 being third side 402 of triangle. The dynamics swing radius 402 is derived from acceleration measurement time line using equation 25. The time space correlation based on the predetermined location defines instantaneous swing radius value required to define all angles of the right triangle including angle 2001 that defines swing plain angle to ground.

Figure 21:
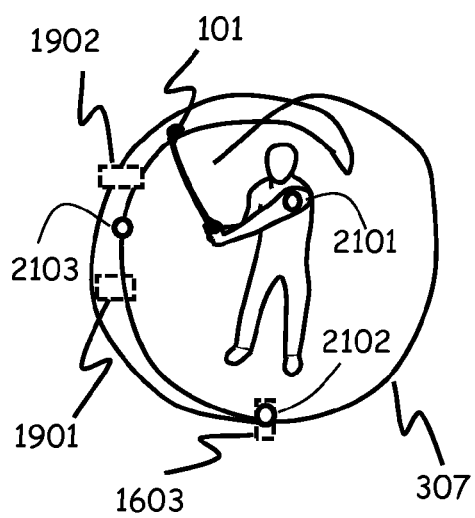
FIGS. 21 and 21A show three points that are used in defining a swing plane for club head travel in different parts of swing
Figure 21A:
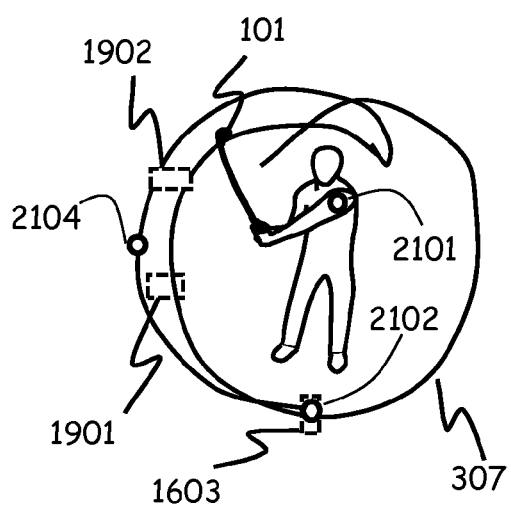

As shown in FIGS. 21 and 21A, the time space correlation of embodiment three enables the calculation of swing plane directly relative to predetermined locations references and shoulder height. The swing plane is determined with three points which include the golfer's shoulder height to the ground as a first point, a predetermined location near the ground as a second point and the swing path point that occurs as the club head passed between two other predetermined locations defining the third point. As an example, using multiple predetermined locations such as those in FIGS. 21 and 21A, two different swing planes can be determined, one for the backswing and one for the power-stroke or down swing. As shown in FIG. 21A the swing plane corresponding to the backswing portion of the swing is determined by defining the spatial location of second point 2102 near the predetermined location 1603 and the spatial location of the third point 2104 being determined by the ratio the ratio of RSSI measurements defining club head location point 2104 on the club head travel path as club head passes between predetermined locations 1901 and 1902. The first point 2101 is defined by the predefined input of golfer's shoulder height and two instantaneous swing radius values on swing radius time line further corresponding to the club head passing through the second point 2102 and third points 2104. The three points define the spatial plane of the backswing. Similarly, as shown in FIG. 21 the swing plane associated with club head travel and during the power-stroke is defined by the three points 2101, 2102 and 2103.

The described invention that includes the use receiver signal strength measurements to create a spatial relationship to a measurement time line can be utilized with any other type of sensor measurement taken on the same time line. Similar to the club head module measurements recited above using three orthogonal acceleration measurements, the RSSI measurements time line can be synchronized with measurement time lines created by any combination of any type of sensor devices. For example, a RSSI measurements time line can be synchronized with measurement time lines created by a single sensor device or combination of sensor devices of varied types that measure motional and or dynamics orientation characteristics from the group of: accelerometer(s), gyroscope(s) and magneto resistive device(s) that can be incorporated into the club heads module. These sensors can be further enhanced with additional spatial cross correlation with optical sensors at the club head module that can detect proximity to fixed light sources at predetermined locations near the swing path.

Further, another embodiment uses RSSI measurements made at the club head or RSSI measurements made at a predetermined location from radio waves transmitted from the club head (club head module) that are synchronized with any type of sensor devices located anywhere on or in the golf club that is not limited to the club head. The benefits of this are the ability of relating all measurements time lines made anywhere on or in the golf club to a spatial reference of the club head during a golf swing. The sensors that may be used, but are not limited to include: accelerometer(s), gyroscope(s), magneto resistive devices, pressure sensors, strains sensors and impact sensors. An example could be, the club head module contains accelerometers to measure club head motion, the shaft has strain gages attached to measure flex, the upper part of the shaft just below the grip has gyroscopes attached to measure shaft rotation at that part of the shaft and the grip has pressure sensors to measure grip strength pressure. All of these sensors may be electrically connected to the central electronics that may be located in the club head module and all measurements synchronized with the RSSI measurement time line that define the spatial relationship to a predetermined location of the club head on that time line.

Although specific embodiments of the invention have been disclosed, those having ordinary skill in the art will understand that changes can be made to the specific embodiments without departing form the spirit and scope of the invention. The scope of the invention is not to be restricted, therefore, to the specific embodiments. Furthermore, it is intended that the appended claims cover any and all such applications, modifications, and embodiments within the scope of the present invention.

I claim:

1. A golf club head module configured to be attachable to and detachable from a golf club head, the golf club head module comprising:
    a circuit configured to measure receiver signal strength of a received radio wave signal along a non-linear travel path of the golf club module, the radio wave signal being received from an external device, the signal strength being measured at least at first and second times along the club head travel path;
    at least one sensor configured to measure additional attribute data along the non-linear travel path of the golf club head module at the first and second times, the additional attribute data including at least one of optical signals, magnetic fields, electric fields, acceleration, and orientation changes; and
    a transmission device configured to transmit synchronous time-aligned receiver signal strength and additional attribute data for the first and second times to the external device for analyzing the non-linear travel path of the golf club head module.

2. The golf club head module of claim 1, wherein analyzing the non-linear club head travel path includes determining lowest and highest signal strength time points, and using the highest and lowest signal strength time points to define a space-time relationship of the club head in conjunction with time-aligned attribute data.

3. The golf club head module of claim 2, wherein defining the space-time relationship includes determining an anticipated ball location.

4. The golf club head module of claim 1, wherein the additional attribute data indicates a perturbation caused by the golf club head impacting an object.

5. The golf club head module of claim 1, wherein the additional attribute data indicates a radial centrifugal inertial component that is separate from a linear spatial translation component.

6. The golf club head module of claim 5, wherein the additional attribute data indicates the radial centrifugal inertial component along each of three measured axis.

7. The golf club head module of claim 1, wherein the time-aligned signal strength and additional attribute data indicate a trigger point at the first time that defines a transition between a back swing segment and a reversal segment of the non-linear club head travel path.

8. The golf club head module of claim 1, wherein the transmission device transmits the time-aligned signal strength and additional attribute data to the external device wirelessly.

9. A golf club measurement system comprising:
    a) a club head module comprising:
        i) a circuit configured to measure receiver signal strength of a received radio wave signal along a non-linear travel path of the club head module, the radio wave signal being received from an external device, the signal strength being measured at least at first and second times along the club head travel path; and
        ii) at least a first sensor configured to measure additional attribute data along the non-linear travel path of the club head module at the first and second times, the additional attribute data including at least one of optical signals, magnetic fields, electric fields, acceleration, and orientation changes;
    b) a shaft module that comprises at least a second sensor from the group of accelerometers and gyroscopes; and
    c) a transmission device configured to transmit synchronous time-aligned receiver signal strength and additional attribute data to the external device for analyzing the non-linear travel path of the golf club head module.

10. The golf club measurement system of claim 9, wherein analyzing the non-linear club head travel path includes determining lowest and highest signal strength time points, and using the highest and lowest signal strength time points to define a space-time relationship of the club head in conjunction with time-aligned attribute data.

11. The golf club measurement system of claim 10, wherein defining the space-time relationship includes determining an anticipated ball location.

12. The golf club measurement system of claim 9, wherein the additional attribute data indicates a perturbation caused by the golf club head impacting an object.

13. The golf club measurement system of claim 9, wherein the additional attribute data indicates a radial centrifugal inertial component that is separate from a linear spatial translation component.

14. The golf club measurement system of claim 13, wherein the additional attribute data indicates the radial centrifugal inertial component along each of three measured axis.

15. The golf club measurement system of claim 9, wherein the time-aligned signal strength and additional attribute data indicate a trigger point at the first time that defines a transition between a back swing segment and a reversal segment of the non-linear club head travel path.

16. The golf club measurement system of claim 9, wherein the transmission device transmits the time-aligned signal strength and additional attribute data to the external device wirelessly.

17. The golf club measurement system of claim 9, wherein first and second modules transmit time-aligned data from the first and second sensors to the external device for measuring shaft rotation and shaft flex.

* * * * *